US012571683B2

(12) United States Patent
Urklinski et al.

(10) Patent No.: US 12,571,683 B2
(45) Date of Patent: Mar. 10, 2026

(54) ELEVATED TEMPERATURE SCREENING SYSTEMS AND METHODS

(71) Applicant: FLIR Systems AB, Täby (SE)

(72) Inventors: Erik Adam Urklinski, Täby (SE); Anton Löf, Täby (SE)

(73) Assignee: FLIR Systems AB, Täby (SE)

( * ) Notice: Subject to any disclaimer, the term of this patent is extended or adjusted under 35 U.S.C. 154(b) by 354 days.

(21) Appl. No.: 17/988,639

(22) Filed: Nov. 16, 2022

(65) Prior Publication Data

US 2023/0079693 A1    Mar. 16, 2023

Related U.S. Application Data

(63) Continuation of application No. PCT/US2021/035023, filed on May 28, 2021.
(Continued)

(51) Int. Cl.
*G01J 5/00*        (2022.01)
*A61B 5/01*        (2006.01)
(Continued)

(52) U.S. Cl.
CPC .............. *G01J 5/0025* (2013.01); *A61B 5/01* (2013.01); *G01J 5/025* (2013.01); *G01J 5/07* (2022.01);
(Continued)

(58) Field of Classification Search
CPC .. G01J 5/0025; G01J 2005/0077; G01J 5/025; G01J 5/07; G01J 5/0859;
(Continued)

(56) References Cited

U.S. PATENT DOCUMENTS 10,157,477 B2 *  12/2018  Chen ...................... G06V 10/56
11,875,544 B2 *   1/2024  Richards ................ G06V 10/82
(Continued)

FOREIGN PATENT DOCUMENTS

KR          10-1165415 B1    7/2012
KR      10-2013-0066759 A    6/2013
(Continued)

OTHER PUBLICATIONS

IPhone X Tip. iPhone X Face ID; Setup, Unlocking, and Attention Options. YouTube. Uploaded by PhotoJoseph, Nov. 2, 2017 (Year: 2017).*
(Continued)

*Primary Examiner* — Chan S Park
*Assistant Examiner* — Chandhana Pedapati
(74) *Attorney, Agent, or Firm* — Haynes and Boone, LLP

(57)        ABSTRACT
Systems and methods include an infrared camera configured to capture an infrared image of a scene, a display configured to display a portion of the captured infrared image and at least one graphic indicia to guide a person being scanned, and a logic device configured to scan a region of interest using an infrared camera, detect a person in the region of interest, instruct the person to move into a scanning position, initiate temperature scanning of person if scanning criteria is satisfied, determine temperature of the person and compare to at least one temperature threshold, and perform a task associated with determined temperature. The system may further comprise a dual-image camera comprising the infrared camera and a visible image camera, wherein the dual-image camera comprises a beamsplitter arranged to reflect visible light towards the visible image camera and pass through an infrared image to the infrared camera.

20 Claims, 36 Drawing Sheets

2000

2010
Instruct user to proper position in front of the infrared camera, including face detection and visual guides to direct the user where to move 2020
Instruct user to remove obstructing apparel, and track compliance with the instruction 2030
Verify that scanning criteria is satisfied and initiate scan 2040
Determine user temperature and compare to one or more thresholds 2050
Display message and/or perform tasks in accordance with measured temperature

Related U.S. Application Data

(60) Provisional application No. 63/033,126, filed on Jun. 1, 2020.

(51) Int. Cl.

| | |
|---|---|
| *G01J 5/02* | (2022.01) |
| *G01J 5/07* | (2022.01) |
| *G01J 5/08* | (2022.01) |
| *G06T 7/292* | (2017.01) |
| *G06V 10/10* | (2022.01) |
| *G06V 10/25* | (2022.01) |
| *G06V 40/16* | (2022.01) |
| *G06V 40/60* | (2022.01) |
| *H04N 5/33* | (2023.01) |
| *H04N 23/11* | (2023.01) |

(52) U.S. Cl.

CPC ............ *G01J 5/0859* (2013.01); *G06T 7/292* (2017.01); *G06V 10/10* (2022.01); *G06V 10/25* (2022.01); *G06V 40/16* (2022.01); *G06V 40/161* (2022.01); *G06V 40/67* (2022.01); *H04N 5/33* (2013.01); *H04N 23/11* (2023.01); *G01J 2005/0077* (2013.01); *G06T 2207/10048* (2013.01); *G06T 2207/30201* (2013.01)

(58) Field of Classification Search

CPC .... G01J 5/53; G01J 5/026; G01J 5/047; G01J 5/0846; A61B 5/01; A61B 5/70; A61B 5/015; G06V 10/143; G06V 40/10; G06V 40/1365; G06V 10/10; G06V 10/25; G06V 40/16; G06V 40/161; G06V 40/67; H04M 2250/52; G06T 7/292; G06T 2207/10048; G06T 2207/30201; G06T 7/74; G06T 2207/10024; G06T 2207/20081; G06T 2207/20084; G06T 2207/30196; G06T 7/337; H04N 5/33; H04N 23/11; H04N 23/23

See application file for complete search history.

(56) References Cited

U.S. PATENT DOCUMENTS

| | | | | |
|---|---|---|---|---|
| 2004/0005086 | A1* | 1/2004 | Wolff .................. | G06V 40/161 |
| | | | | 382/284 |
| 2007/0153871 | A1* | 7/2007 | Fraden .................. | A61B 5/015 |
| | | | | 374/121 |
| 2008/0194983 | A1* | 8/2008 | Laurence .............. | G01J 5/0821 |
| | | | | 374/E11.003 |
| 2009/0249486 | A1* | 10/2009 | Johnson ........... | H04N 21/45452 |
| | | | | 726/26 |
| 2013/0235901 | A1* | 9/2013 | Shin .......................... | G01J 5/07 |
| | | | | 374/121 |
| 2017/0270348 | A1* | 9/2017 | Morgana .............. | H04N 23/611 |
| 2018/0232581 | A1* | 8/2018 | Reinpoldt .............. | G06V 20/52 |
| 2018/0313695 | A1* | 11/2018 | Shim ..................... | G01J 5/0859 |
| 2020/0372743 | A1* | 11/2020 | Miller ................... | G07C 9/257 |
| 2021/0304537 | A1* | 9/2021 | Reed ...................... | G06F 18/22 |
| 2023/0054197 | A1* | 2/2023 | Richards .............. | G01J 5/0806 |

FOREIGN PATENT DOCUMENTS

| | | | | |
|---|---|---|---|---|
| KR | 10-2017-0050936 A | | 5/2017 | |
| KR | 10-2017-0050954 A | | 5/2017 | |
| KR | 10-2020-0041458 A | | 4/2020 | |
| WO | WO-2019016406 A1 * | | 1/2019 | .............. G09B 5/02 |

OTHER PUBLICATIONS

A. Somboonkaew et al., "Mobile-platform for automatic fever screening system based on infrared forehead temperature," 2017 Opto-Electronics and Communications Conference (OECC) and Photonics Global Conference (PGC), Singapore, 2017, pp. 1-4, doi: 10.1109/OECC.2017.8114910. (Year: 2017).*

Kenmoo223, "Urovo H1000 Face Recognition with Temperature Measuring System Terminal", Apr. 13, 2020. Retrieved from Internet: <https://www.youtube.com/shorts/epxz109kHrg>. (Year: 2020).*

Enster, "Face recognition and Temperature Detection AI Smart Camera", Mar. 28, 2020. Retrieved from Internet: <https://www.youtube.com/watch?v=xqP3tPGwmnw>. (Year: 2020).*

SelenaSuidlintech (Temperature Measurement and Face Recognition Integrated Device/ infrared thermometer-English/Turkish, Apr. 28, 2020. Retrieved from Internet: <https://www.youtube.com/shorts/caaVtDe-o8U>) (Year: 2020).*

Pipl Systems (Real body temperature measurement solution tested, Mar. 25, 2020. Retrieved from Internet: (https://www.youtube.com/watch?v=iTJAHIpFksM>) (Year: 2020).*

Soonmin Hwang et al: "Multi spectral pedestrian detection: Benchmark dataset and baseline", Proceedings of the IEEE Conference on Computer Vision and Pattern Recognition (CVPR), Jun. 1, 2015, pp. 1037-1045, XP055769507, DOI: 10.1109/CVPR. 2015.7298706 ISBN: 978-1-4673-6964-0.

Caterpillar, "CAT S61 Bigger. Better. Bolder." CAT S61 Smartphone Specification Sheet, Jan. 2020, 2 pages, Caterpillar, Irving, Texas, United States of America.

Seek Thermal, "Seek Scan Simple Screening for Safer Communities", Seek Scan Specification Sheet, Sep. 2020, 3 pages, Seek Thermal, Santa Barbara, California, United States of America.

Yoon In-Ho, Screen captures from YouTube short video clip entitled "Facial recognition temperature measurement CCTV panel 1," Yoon In-ho, 1 page, May 8, 2020. Retrieved from Internet: <https://www.youtube.com/shorts/SpvH8B2QPhc>.

\* cited by examiner

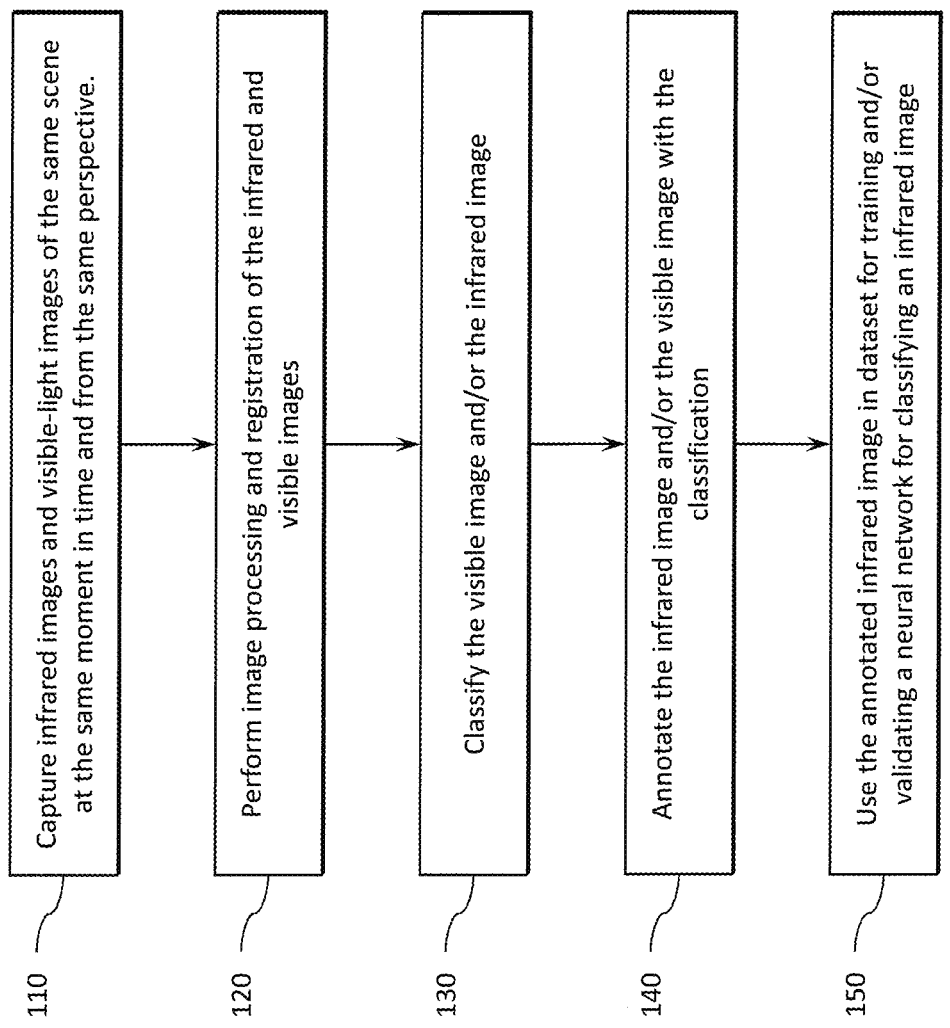

100

110 — Capture infrared images and visible-light images of the same scene at the same moment in time and from the same perspective.

120 — Perform image processing and registration of the infrared and visible images 130 — Classify the visible image and/or the infrared image 140 — Annotate the infrared image and/or the visible image with the classification 150 — Use the annotated infrared image in dataset for training and/or validating a neural network for classifying an infrared image

**Blackbody Temperature Versus In-Band Radiance
(7-14 Microns LWIR Band)**

Y = 8869.3x-28.86
$R^3$ = 0.9996

Apparent Temperature (Degrees C)

In-Band Radiance (Watts/Square cm/sr)

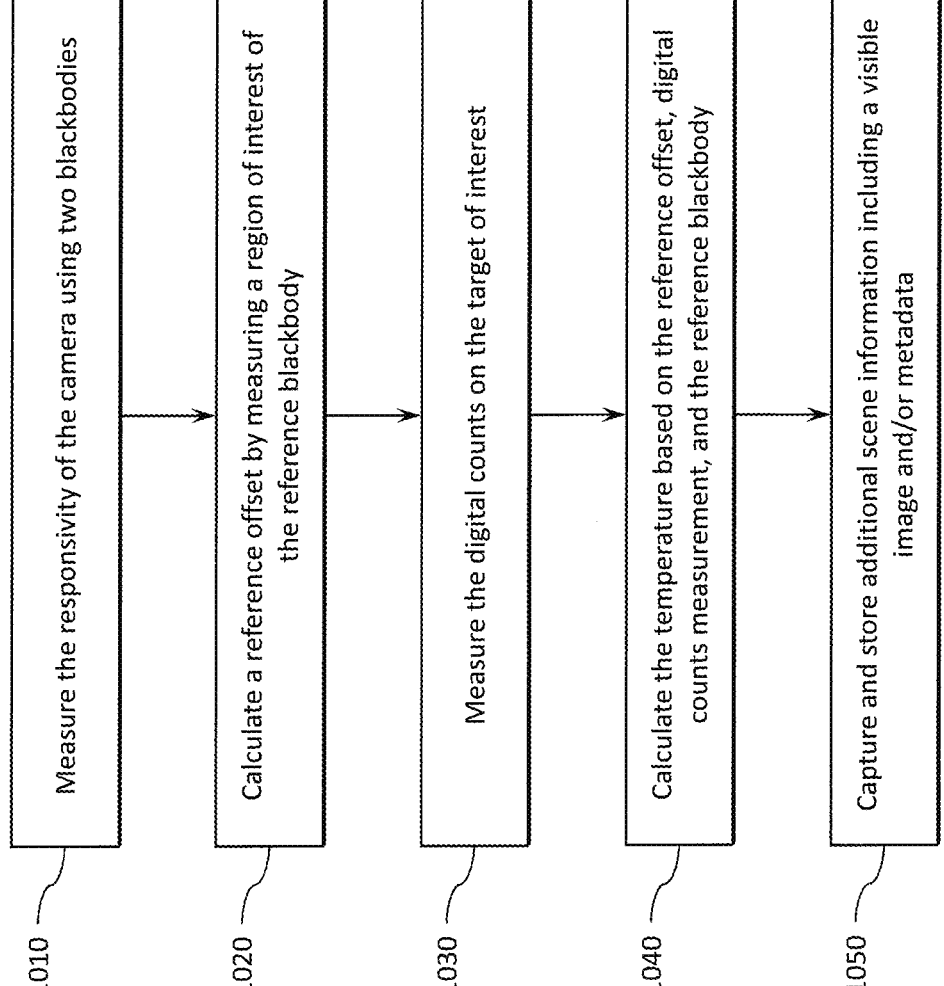

1000

1010 — Measure the responsivity of the camera using two blackbodies

1020 — Calculate a reference offset by measuring a region of interest of the reference blackbody 1030 — Measure the digital counts on the target of interest 1040 — Calculate the temperature based on the reference offset, digital counts measurement, and the reference blackbody 1050 — Capture and store additional scene information including a visible image and/or metadata

Cover Over Optics and Housing

1704

1712

Beamsplitter

LWIR
640
14mm 1720                    1710    1702

1800

1800

2000 ⬎

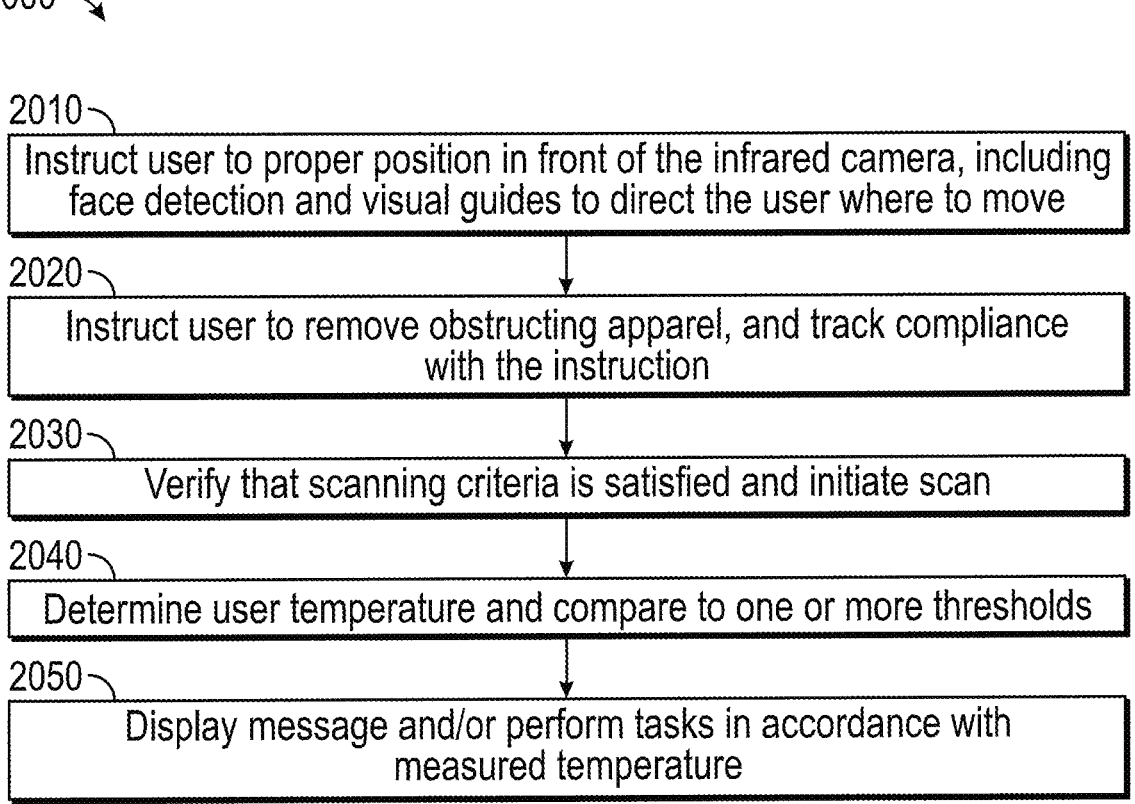

2010 ⬎
Instruct user to proper position in front of the infrared camera, including face detection and visual guides to direct the user where to move 2020 ⬎
Instruct user to remove obstructing apparel, and track compliance with the instruction 2030 ⬎
Verify that scanning criteria is satisfied and initiate scan 2040 ⬎
Determine user temperature and compare to one or more thresholds 2050 ⬎
Display message and/or perform tasks in accordance with measured temperature

LIVE     DEVICES     LIBRARY

Plug in camera

Plug in your camera in your computer using a USB cable

....

BACK     NEXT

2100

LIVE     DEVICES     LIBRARY

System Setup

XXXX XXXX XXXXXXXXXX XXXX
XXXX XXXX XXXXXXXX XXXX
XXXXXXXXXX..

....

NEXT

2130
LIVE  DEVICES  LIBRARY
X
2m
Distance
XXXX XXXX XXXXXXXXX XXXX
XXXX XXXX XXXXXXXX XXXX
XXXXXXXX .
. . . .
BACK     NEXT
FIG. 21D
2120
LIVE  DEVICES  LIBRARY
Plug in camera
Plug in your camera in your computer using a USB cable
. . . .
BACK     NEXT
FIG. 21C
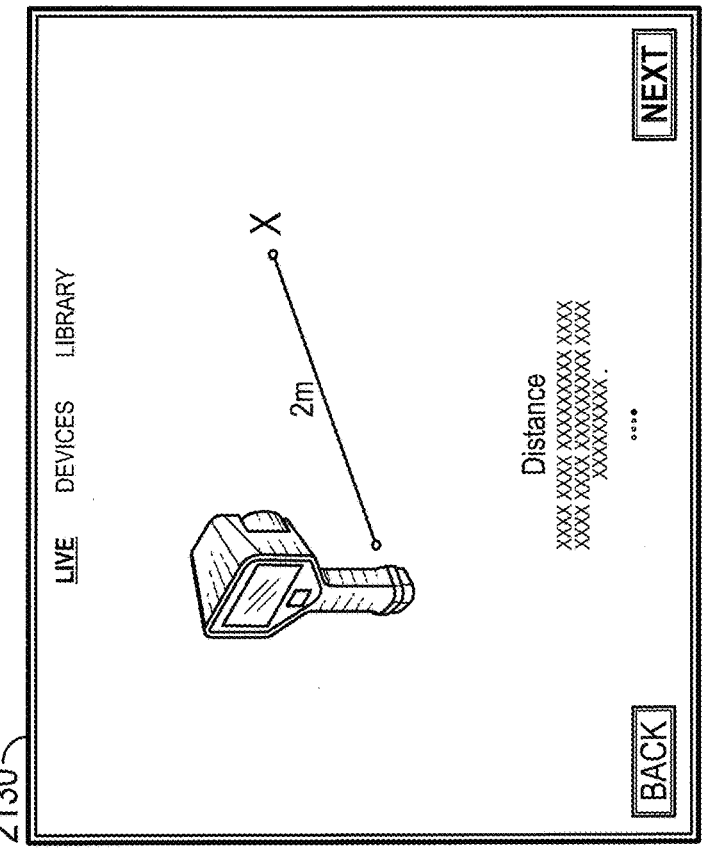
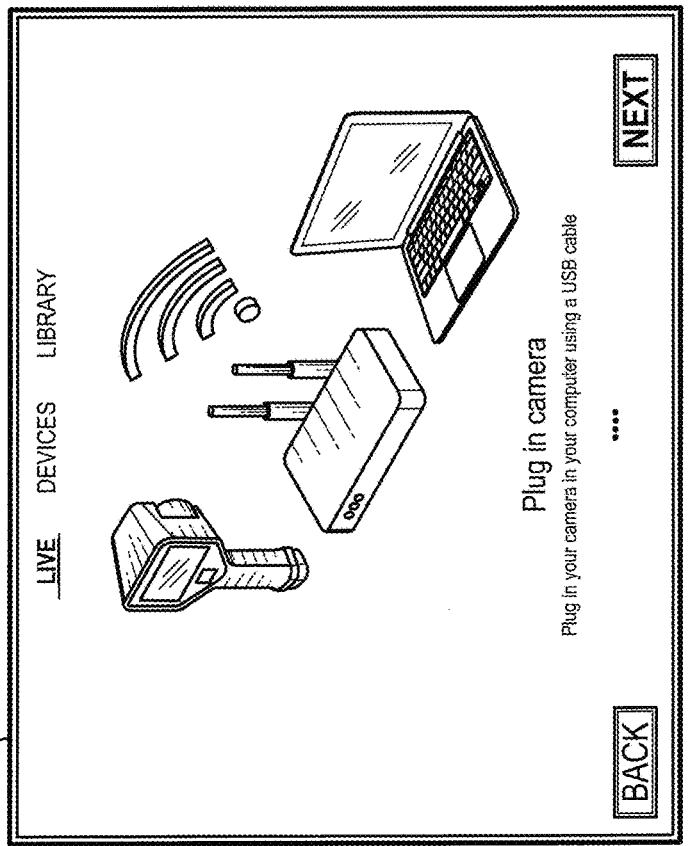

2150

2152
2154

LIVE    DEVICES    LIBRARY

NEXT

Region of intrest [ROI]

set a region where faces can be detected this can be used to to avoid pacing up unwanted people on the side or in the back ground.

....

BACK

2140

LIVE    DEVICES    LIBRARY

NEXT

□ AUTO FOCUS camera focus

XXXX XXXX XXXXXXXXX XXXX
XXXX XXXX XXXXXXX XXXX

....

BACK

ELEVATED TEMPERATURE SCREENING SYSTEMS AND METHODS

CROSS-REFERENCE TO RELATED APPLICATIONS

This application is a continuation of International Patent Application No. PCT/US2021/035023 filed May 28, 2021 and entitled "ELEVATED TEMPERATURE SCREENING SYSTEMS AND METHODS," which claims priority to and the benefit of U.S. Provisional Patent Application No. 63/033,126 filed Jun. 1, 2020 and entitled "ELEVATED TEMPERATURE SCREENING SYSTEMS AND METHODS," all of which are hereby incorporated by reference in their entirety.

TECHNICAL FIELD

One or more embodiments of the present disclosure relate generally to thermal imaging systems, and more particularly, for example, to systems and methods for detecting body temperature and/or skin temperature that is elevated.

BACKGROUND

In the field of image processing, there is an ongoing need for efficient and reliable ways to analyze and process images captured by imaging devices. Conventional systems may include machine learning systems trained on labeled image datasets. However, training and validating these systems are subject to error when the images are difficult to accurately label. For example, thermal images present difficulties because human operators, even experts highly trained in the identification of objects in thermal images, can have trouble deciding how to label objects in a thermal scene. The difficulties arise because many objects can and do look quite different in the thermal IR bands than they do in the visible band. In view of the foregoing, there is a continued need in the art for improved image processing systems and methods.

SUMMARY

The present disclosure provides various embodiments of systems and methods for detecting temperature of an object in an image, such as measuring elevated body temperature (EBT) and/or skin temperature that is elevated, for fever detection. In some embodiments, an infrared camera is used to measure skin temperature without physical contact with the subject, which is an important aspect of systems used for detecting potentially infectious diseases. A person with a fever will have an elevated core body temperature and under certain conditions, this elevated temperature can manifest itself as skin having an elevated temperature, particularly on facial skin near the tear duct (canthus), an area of the face with a high degree of blood flow. This canthus can be identified in an image and the measured surface temperature may correspond to the user's body temperature (e.g., the canthus may be a few degrees cooler than the core body temperature).

Various systems and methods are provided for annotating infrared images for use in machine learning applications. In some embodiments, a dual-band camera rig composed of a visible-light camera (e.g., producing an RGB image) and an infrared camera (e.g., a thermal IR camera) is used to acquire images that are spatially and temporally registered to a high degree of precision. The RGB images are annotated manually and/or automatically (e.g., by human technicians, automatic object recognition software, etc.). The annotations are then transferred to the infrared images, which themselves are much more difficult to annotate, since some edge details as well as color that gives context are not present in the thermal IR images.

In some embodiments, systems and methods provide improved accuracy and consistency for skin temperature measurement. The system allows an untrained person to be guided to perform a thermal imaging skin temperature scan and interpret the result without the need of education or any prior knowledge about thermodynamics or infrared technology. With the help of instructions—text, sound and overlay graphics—the user receives relevant information about how to proceed with the scan to get a consistent and accurate result.

Various embodiments also aid in the set-up of an elevated body temperature system, guiding the user through the process of installing the system to give a consistent and accurate result and therefore being able to avoid and/or reduce false negatives. In some embodiments, step-by-step guidance is provided to lower the threshold of use, enabling various people, companies, organizations, stores, or facilities to utilize thermal imaging for detecting skin temperature that is elevated. Various advantages of the systems and methods disclosed herein include simplicity, a sophisticated graphical user interface, and methods orchestrated in such a way that the system can be used and deployed with no or limited requirements of certain knowledge or context.

The scope of the disclosure is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 1 is a flow chart of an example process for training a machine learning system for infrared image classification, in accordance with one or more embodiments of the present disclosure.

FIG. 10 is a flow diagram illustrating a process for operating a thermal imaging system using one blackbody, in accordance with one or more embodiments.

FIG. 20 is a flow diagram illustrating a process for detecting elevated body temperature, in accordance with one or more embodiments.

FIGS. 21A, 21B, 21C, 21D, 21E, and 21F, illustrate screens of a system set up process, in accordance with one or more embodiments.

Embodiments of the disclosure and their advantages are best understood by referring to the detailed description that follows. It should be appreciated that like reference numerals are used to identify like elements illustrated in one or more of the figures.

DETAILED DESCRIPTION

Figures 2A, 2B:
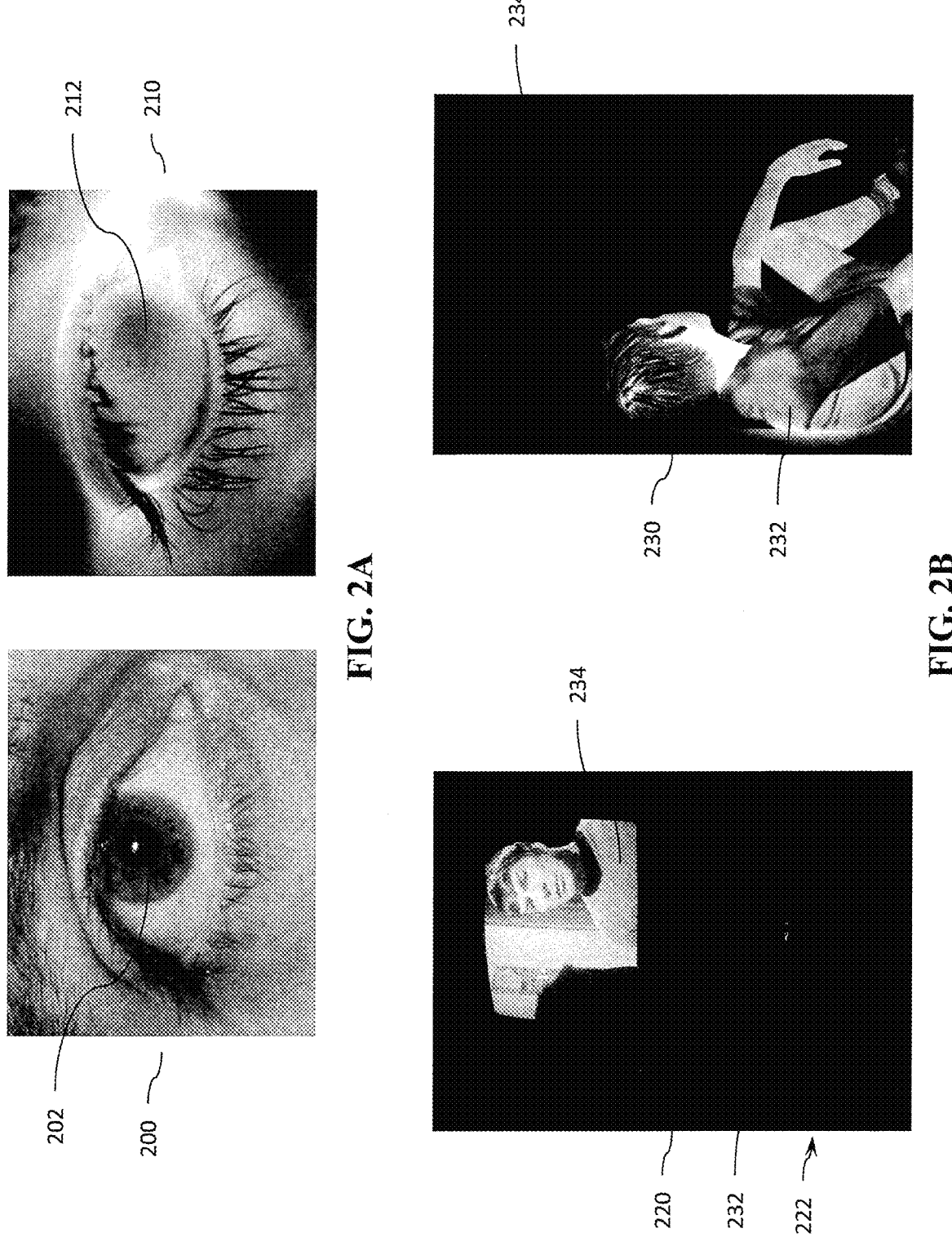
FIGS. 2A, 2B, 2C, and 2D illustrate differences between visible and infrared images, in accordance with one or more embodiments of the present disclosure.

The present disclosure provides systems and methods for measuring elevate body temperature. In some embodiments, systems and methods include a dual band image capture system. When one is measuring elevated body temperature using thermal imaging, it may be useful to have a visible-light image of the subject for reference. This reference image can be used to identify an object (e.g., a person to be measured), since it may be difficult to identify a person using a thermal image. It is also useful for the correlation of anatomical structures such as the inner corner of the eye (canthus) in both the visible and the thermal image when one is making a study of the hottest part of a person's face. In various embodiments, a dichroic beamsplitter is used to separate light by wavelength, making it possible to overlay visible and infrared image streams while minimizing parallax. In the disclosure provided herein, a dual-band training system will be first be described, followed by an example implementation of a trained dual image capture system.

The present disclosure also solves other problems within the topic of scanning for elevated skin and/or body temperature using infrared technology. For example, one problem solved is enabling and instructing virtually any user to perform a self-evaluating skin temperature scan using infrared technology, including user who may not have prior knowledge of thermal imaging. Additionally, embodiments of the present disclosure aim to guide a user in how to set up the self-scanning system with the correct settings and circumstances, to more efficiently perform as accurate and consistent measurements as possible. Embodiments also incorporate post-analysis aspects of tracking the result of scanned individuals, enabling a historical trend of the recorded temperature measurements. The present disclosure enables facilities to be equipped with a self-scanning system that can detect skin temperature of people entering the building, which ultimately can aid in the decision of if the scanned individual should be allowed in our not.

Dual-Band Temperature Detection Training Systems and Methods

The present disclosure provides systems and methods for annotating infrared images for use in machine learning applications. In some embodiments, a dual-band camera rig composed of a visible-light camera (e.g., producing an RGB image) and an infrared camera (e.g., a thermal IR camera) is used to acquire images that are spatially and temporally registered to a high degree of precision. The RGB images are annotated manually and/or automatically (e.g., by human technicians, automatic object recognition software, etc.). The annotations are then transferred to the infrared images, which themselves are much more difficult to annotate, since some edge details as well as color that gives context are not present in the thermal IR images.

In order to properly train a convolutional neural network (CNN) for image classification and evaluate the CNN's ability to classify images and the objects in them, the images are labeled with annotations that are used in the training set. In many applications, the annotation is a process where a human operator manually labels objects in an image, for example pedestrians or stop signs in a traffic scene. The CNN is trained with large datasets having thousands of images, for example. The CNN is evaluated based on the correctness of its ability to identify the annotated objects on new images from a test dataset that were not part of the training set.

There is some difficulty, however, in having human operators correctly annotate thermal IR images. For example, a two-year old human being can quite easily identify many objects with a single glance, but even experts highly trained in the identification of objects in thermal images can have trouble deciding how to label objects in a scene. The difficulties arise because many objects can and do look quite different in the thermal IR bands than they do in the visible band. For example, blue eyes do not look blue in a raw thermal image—the iris will be represented with shades of grey. Dark areas in a visible image can look quite bright in a thermal image and vice-versa, which adds to annotation confusion. In some cases, a thermal image can have an object with very high contrast between it and the scene, but very low contrast in the visible band.

An example process for training a machine learning system for infrared image classification in accordance with one or more embodiments will now be described with reference to FIG. 1. In various embodiments, a process 100 includes, in step 110, capturing infrared images (e.g., thermal images) and visible-light images of the same scene at the same moment in time and from the same perspective. In step 120, the two images are registered so that a pixel on one image is registered to the corresponding pixel on the other image, and both pixels are viewing the same position in object space at the same moment in time. In various embodiments, a warping algorithm or other image alignment algorithm can be used.

In step 130, the visible image and/or infrared image are classified. In some embodiments, automatic object classifier application can be run on the visible image and/or thermal image to identify object classifications, object locations, and other object information from the images. In step 140, a human operator reviews the preliminary classifications and decides how to annotate them. In some embodiments, the annotations can be limited to one image, such as the visible image which is more likely to be visually understandable to the user than the infrared image, and then applied to the other image, such as the infrared image. The annotations may include an object location, an object classification and/or other object information.

In step 150, the annotated infrared image is used in a dataset to train and/or validate a machine learning system for classifying an infrared image. In some embodiments, a convolutional neural network (CNN) is trained for image classification and validated to evaluate the CNN's accuracy in classifying images and the objects in them, by using the annotated images to create a training dataset. The annotation process, as discussed above may be part of the CNN training process and may include manual classification where a human operator labels objects in the image by hand, for example pedestrians or stop signs. In some embodiments, human annotations may be assisted by running CNN detectors on the image that provide predictions (automatic or machine annotations) and, instead of starting from scratch, the annotator can then review the predictions and correct them if needed. The CNN is trained with large datasets consisting of thousands of images, and the CNN is evaluated based on the correctness of its ability to identify the annotated objects on new images from a validation dataset that were not part of the training set.

Figures 2C, 2D:
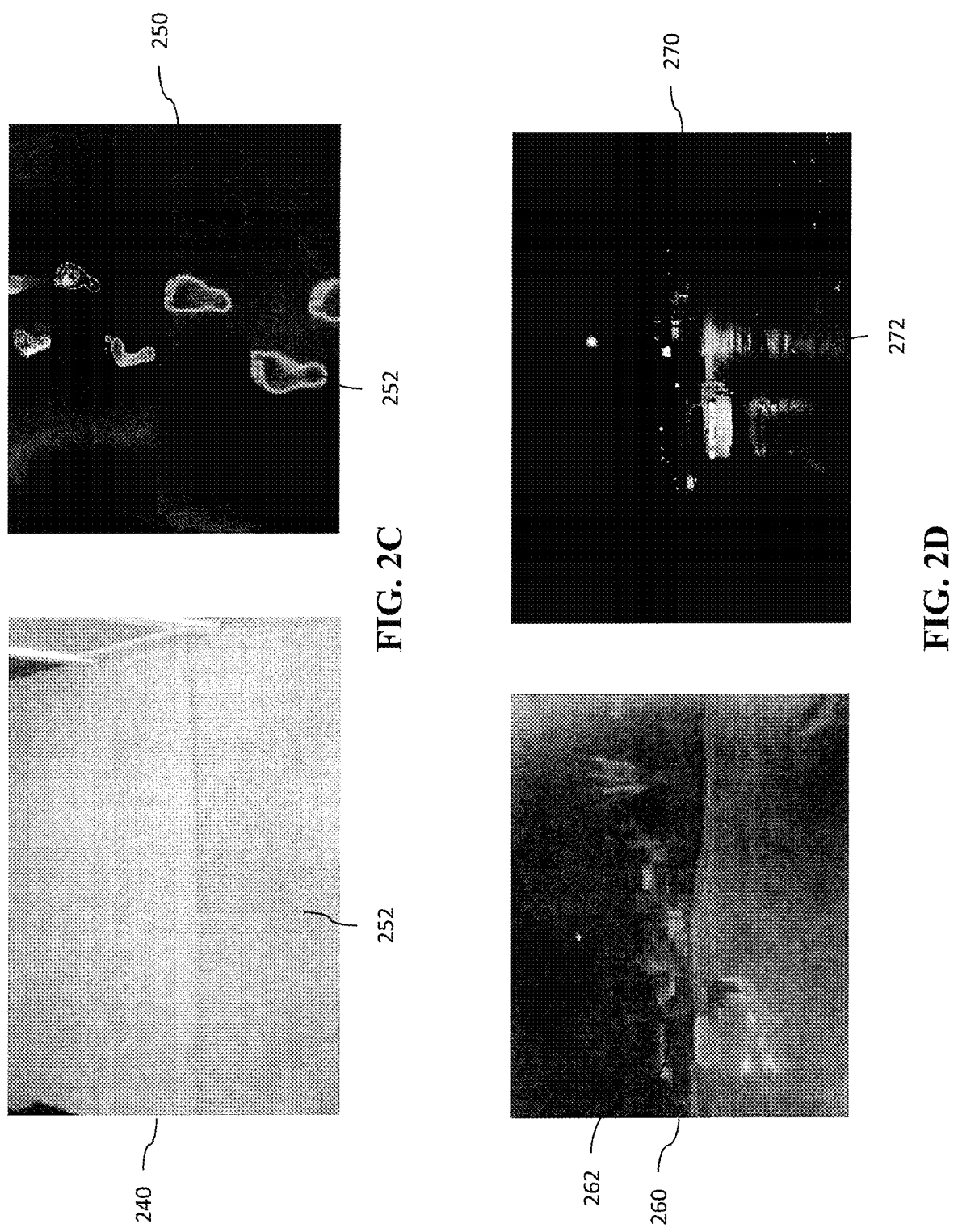

As previously discussed, there is some difficulty in having human operators correctly annotate thermal IR images. A two-year old human being can quite easily identify many objects with a single glance, but even experts highly trained in the identification of objects in thermal images can have trouble deciding how to label objects in a scene. The difficulties arise because many objects can and do look quite different in the thermal IR bands than they do in the visible band. For example, as illustrated in FIG. 2A, blue eyes 202 in a visible image 200 do not look blue in a raw thermal image 210—e.g., the iris may be represented with shades of grey 212 as illustrated. Referring to FIG. 2B, dark areas 222 in a visible image 220 can look quite bright in a thermal image 230 and vice-versa, which adds to annotation confusion. Here the TV 234 is barely discernable in the thermal image 230, just as the boy 232 is bright in the thermal image and barely apparent in the visible-light image. In some cases, a thermal image can have an object with very high contrast between it and the scene, but very low or no contrast in the visible band. Referring to FIG. 2C, for example, a visible image 240 and a midwave IR image 250 of hot footprints 252 illustrate this phenomenon. In this example, the footprints 252 are not visibly identifiable in the visible image 240 but can be seen in the midwave IR image 250.

In various embodiments disclosed herein, a solution is to train and teach the network for thermal image classification in the visible image and apply the annotation results to the thermal images in the training and validation datasets. In some embodiments, the solution includes both visible and thermal image classification, and the results are synthesized into the annotations as appropriate. The datasets include groups of images for training and validating the neural models. The quality of the datasets affects the resulting models, with more accurate datasets providing better quality models. The datasets may include multi-sensor datasets having images in two or more spectrums (e.g., visible, thermal, other spectrums).

When building datasets for multi-sensor training systems, image pairs are selected with accurate correspondence between the frames of the image pairs. As described herein, both spectrum frames may be taken at the same time from the substantially similar perspectives of the captured scene. Another factor that affects training performance is the accuracy of the box or polygon (e.g., the ground truth) that identifies the object to be analyzed.

In some embodiments, a beamsplitter-based camera is employed to with two cameras that are in sync, so frames are captured at the same time. Using this camera reduces the time needed to select and register frames for use in a dataset. The system can select an appropriate data image from one of the spectrums (e.g., a high-quality image appropriate for a test image), and then the corresponding paired image will also be chosen for the dataset, thereby reducing time required to choose frames for the dataset.

After the accurate alignment of the two images (e.g., alignment of the pixels of each image), annotations may be performed on the image that best represents (or shows) the desired object and those annotations can be matched to the image in the other spectrum. This method improves the accuracy of the classification because each spectrum be used to identify the borders of the object.

In some embodiments, the multisensor camera may be combined in a system with a radiometric camera to provide additional functionally that would otherwise be difficult to implement with conventional systems. Pixel-to-pixel alignment allows the CNN models to work in both spectrums to provide the best of each. For example, in an elevated body temperature system, well illuminated objects will go through CNN-visible networks to identify shapes and body parts, then the CNN-thermal networks may be used to identify in these parts the skin and measure the temperature of it. In another example, the system could use visible-light images to find the shape of an object (e.g., a car), and then use thermal images to locate and identify exhaust to determine whether a car is a electrical or gasoline powered vehicle.

In some embodiments, having the pixel-to-pixel alignment allows a direct temperature measurement of each pixel location that is captured in the visible spectrum. Visible-light CNN models can be used for detection of objects and/or objects-parts and the corresponding pixels from the thermal image can provide the temperature information. This system has many advantages, including added privacy in systems in which the visible-light image is used only to facilitate accurate temperature measurements, and is displayed or available for use to further identify a person.

Referring to FIG. 2D, the visible image 270 on the right has been machine annotated, with blue bounding box 272 around a white car, but the car 262 is not annotated in the corresponding thermal image 260. A solution, as disclosed herein, is to capture thermal images and visible-light images of the same scene at the same moment in time and from the same perspective. A warping algorithm or other alignment algorithm can be used to register the two images so that a pixel on one channel is registered to the corresponding pixel on the other channel, and both these pixels are viewing the same position in object space at the same moment in time. A human annotator can compare both images (and automatic image classification results, if available) and decide how to annotate them both. The annotations for one image can then be applied to the other image. This concept can be used to improve the auto-classification of thermal images using convolutional neural networks which have been trained with visible images. The visible-light image of the pair will be used for this matter, and results will be applicable to the corresponding thermal image.

Another advantage of the present embodiment is that classification can be performed with increased levels of privacy, because a third party can classify the images using visible image data without sharing the private infrared image data. The results can then be applied to the thermal IR images. For the scenes that only reveal context in thermal IR, a second phase may be applied that includes automated thermal image classification and/or human classification, but in general this technique will reduce the effort a lot.

Figure 3:
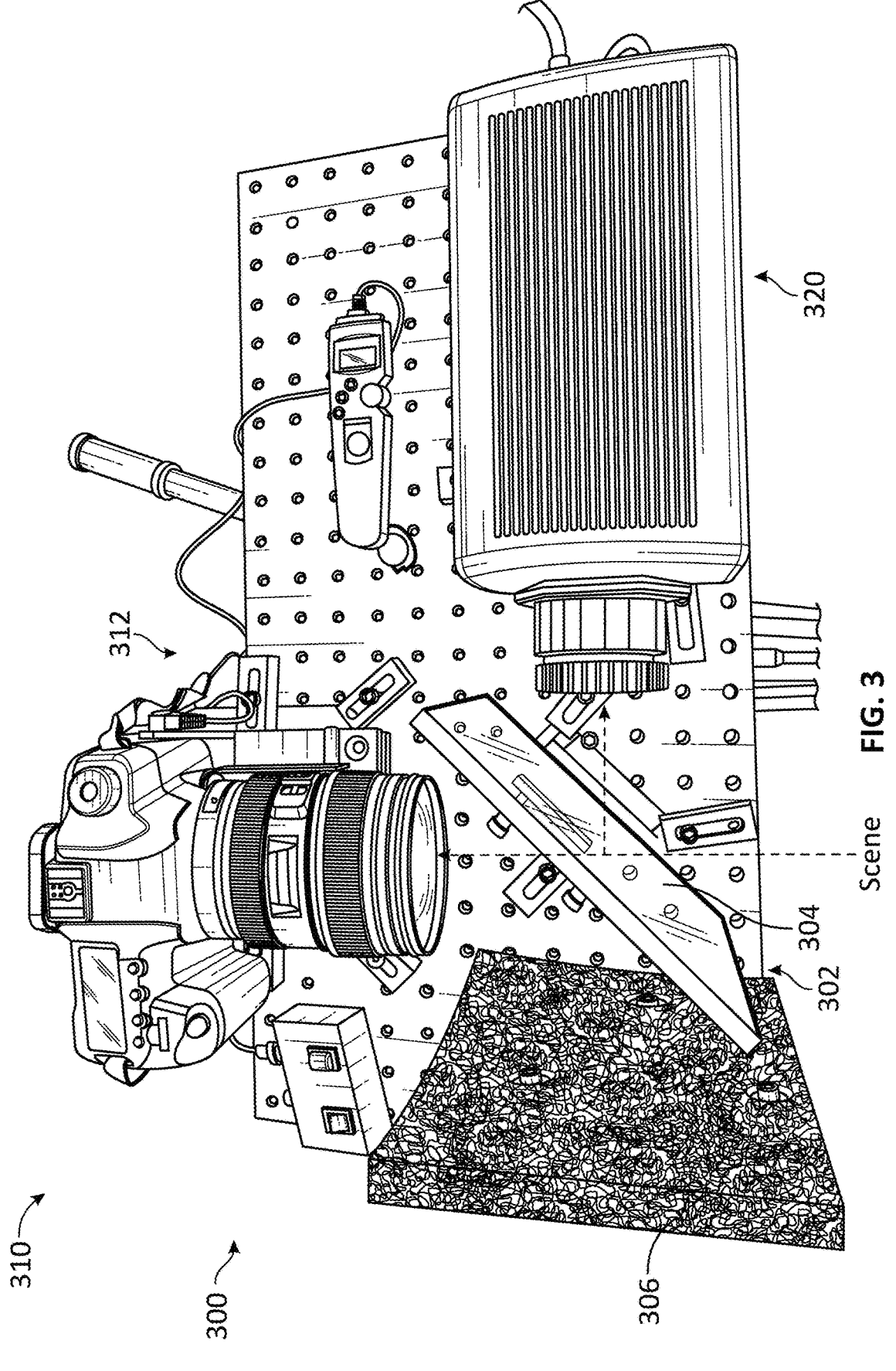
FIG. 3 illustrates a system for generating paired visible-light and infrared dataset images, in accordance with one or more embodiments of the present disclosure.
Figures 4A, 4B, 4C, 4D:
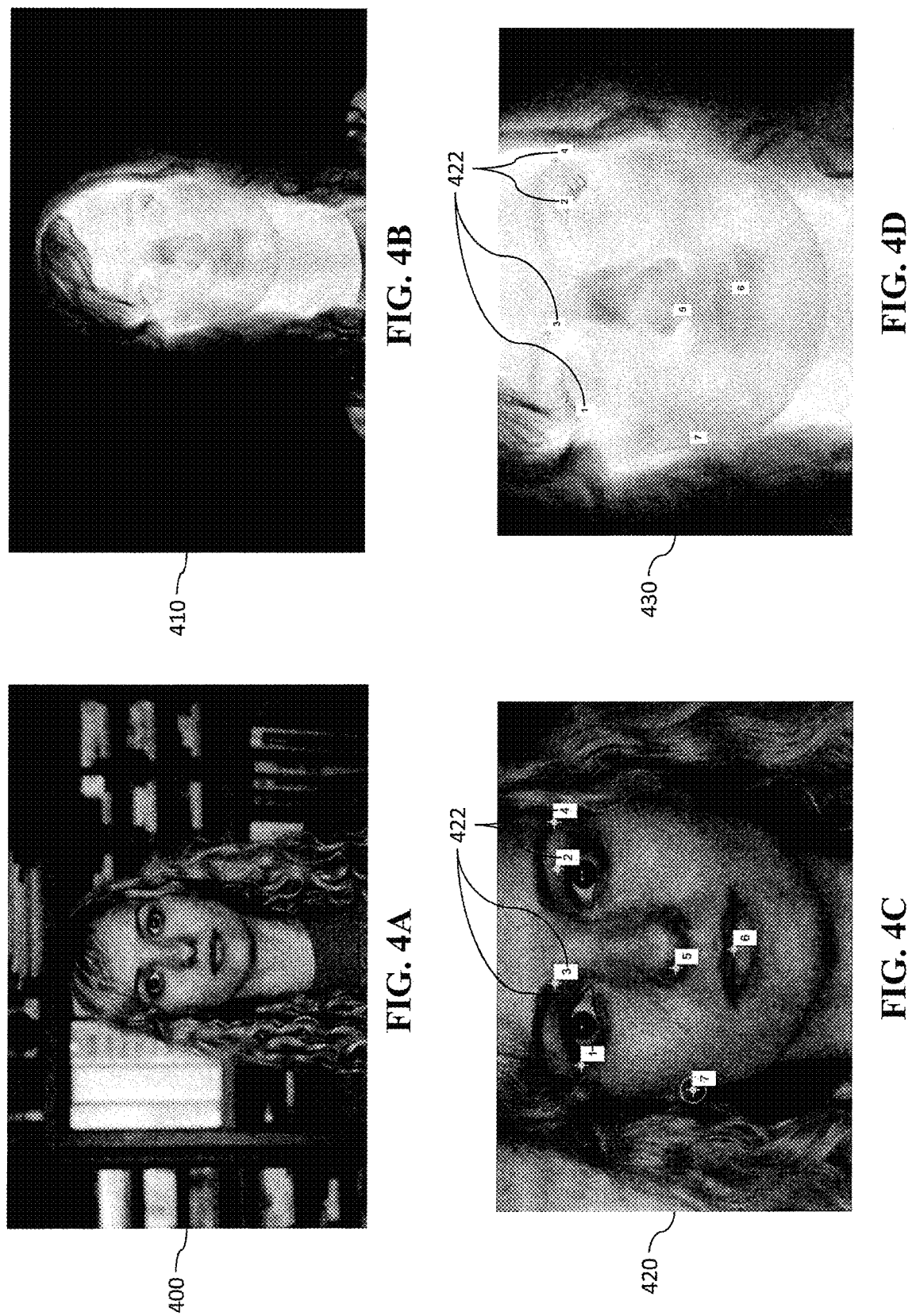
FIGS. 4A, 4B, 4C, 4D, and 4E are example visible and infrared image pairs captured using the system of FIG. 3, in accordance with one or more embodiments of the present disclosure.
Figure 4E:
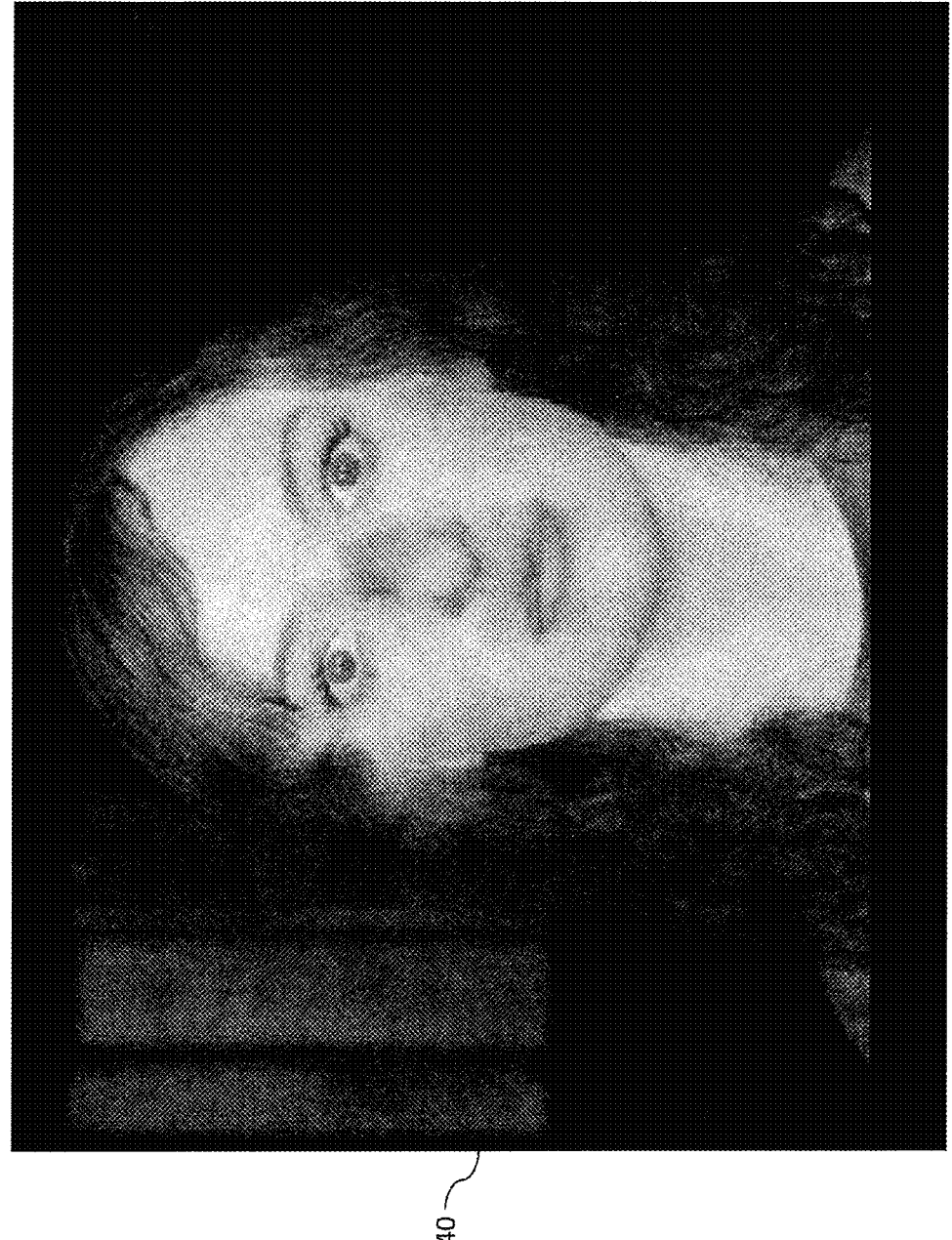

Embodiments of a system for generating dataset images in accordance with the present disclosure are illustrated in FIG. 3. The time synchronization can be accomplished by making one of the cameras trigger the other. An infrared camera 320 (e.g., a high definition midwave infrared camera) is config-ured with synchronous outputs that can be routed into the sync input of a visible-light camera 310. The two cameras are configured to start integration of a scene at the same time (e.g., within a few microseconds), with matched integration times which matches motion blur between the two channels.

Spatial registration can be accomplished with a system 300 that further includes a dichroic beamsplitter 302 which separates visible and infrared radiation from the scene. The visible-light camera 310 and the infrared camera 320 are positioned to receive the separated visible and infrared radiation, respectively. In the illustrated embodiment, the infrared camera 320 is a midwave IR camera that captures a reflection 304 of the scene folded through 90 degrees of angle by the beamsplitter 302 which is viewed by the infrared camera 320 at a 45-degree angle. The visible-light camera 310 looks through the beamsplitter 302 at the scene, which may include an object to detect and classify. In various embodiments, it is desirable for the optical axes of the visible-light camera 310 and the infrared camera 320 to be precisely lined up so that there is negligible perspective change between the two, which allows for the creation of accurately registered images at all distances.

If the two cameras are mounted next to each other, there will be a parallax error between them. The illustrated system 300 eliminates all parallax. The lenses for the two cameras may be selected to match the fields of view between the cameras, and/or adjustments to the captured images (e.g., cropping the larger image) may be performed after image capture. In some embodiments, the cameras are mounted on boresighting mounts 312 that can be adjusted in elevation and azimuth angles. Precision spacers underneath the vis-ible-light camera mount sets the height of the visible-light optical axis above the optical breadboard to be the same as the midwave IR optical axis. A glare stop 306, such as a piece of dark grey foam, is located to the left of the beamsplitter 302 in the illustrated embodiment to reduce reflections of visible-light off the beamsplitter side facing the visible-light camera 310.

As illustrated, the beamsplitter 302 may be implemented as a dichroic beamsplitter made of 0.3" BK7 glass. One side of the glass is coated with a layer of indium tin oxide (ITO) which makes it ~80% reflective in the midwave IR band (3-5 microns in wavelength units), and the other side has a built in visible-light anti-reflective coating. The beamsplitter 302 is also ~90% transparent to visible-light. In various embodi-ments, the beamsplitter 302 may be any beamsplitter that reflects a desired infrared band and is transparent to visible-light to allow for image capture at a quality that satisfies requirements of a particular system implementation.

Referring to FIGS. 4A-E, a pair of images taken with an example system are shown. The two images (such as visible image 400 and infrared image 410) can be spatially regis-tered with high precision with various techniques, including a two-dimensional affine transform which can be defined by control points (such as control points 422 shown in visible image 420 and infrared image 430) that are common to the two images. The affine transform warps the image to correct for differences in the lens distortions and results in precise image registration across the entire field of view. In one approach, the visible image 400 is warped to match the infrared image 410. The control points 422 may be selected in places with high contrast in both images, as shown in visible image 420 and infrared image 430. The resulting overlay image 440 of the two images is shown with a color "map" with the "fixed" midwave IR image shown in green and the moving image shown in purple.

In some embodiments, a registration process can include use of a target that has high-contrast fiducial points distrib-uted over the entire field of view. This can be achieved with an ambient temperature white panel perforated with small holes and backlit with a black-painted heated panel. The affine transform can be determined and used on subsequent images shot with the system, as long as the cameras and beamsplitter assembly all remain locked into the same relative positions.

Figure 5:
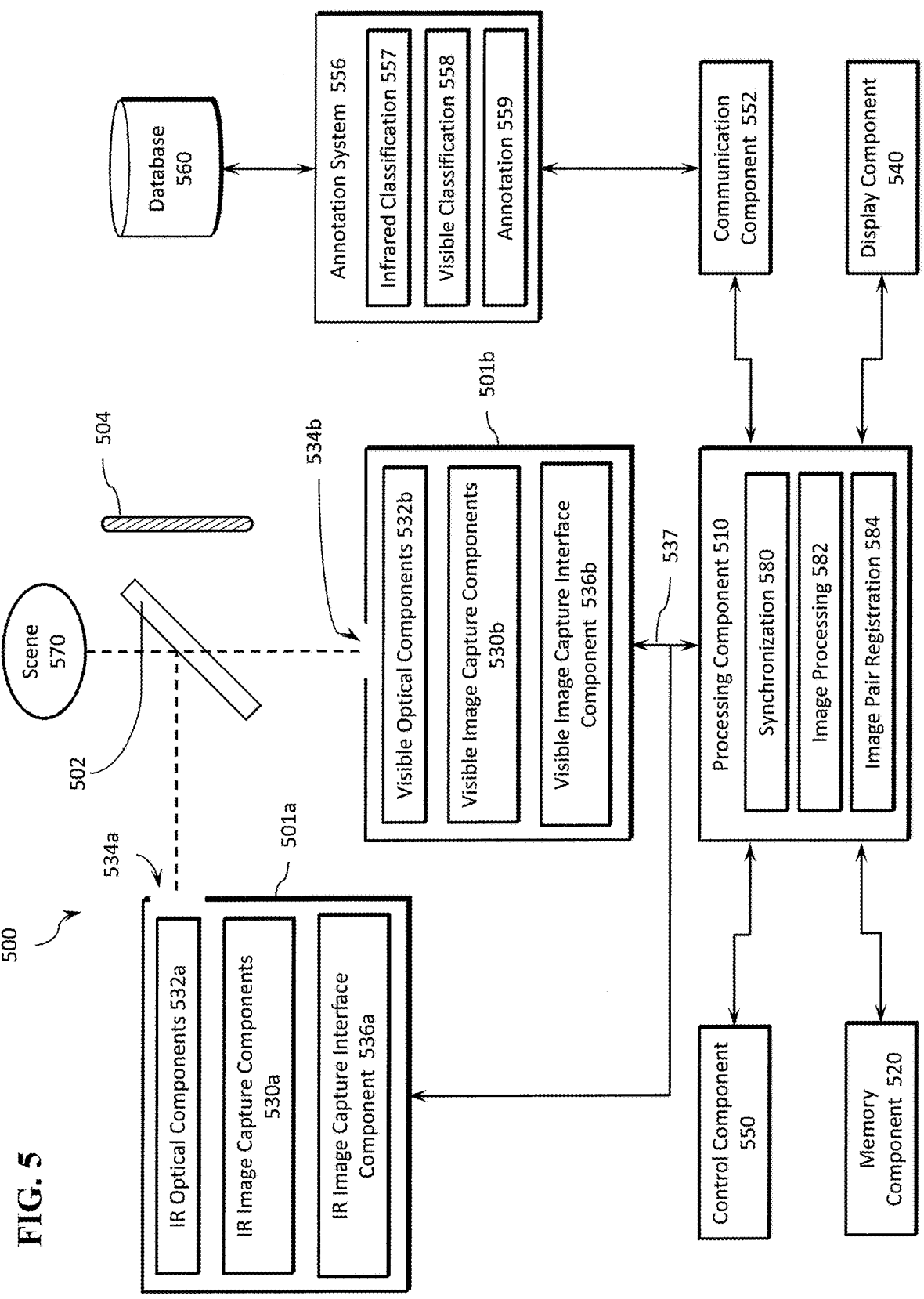
FIG. 5 illustrates an example infrared imaging and annotation system, in accordance with one or more embodiments of the present disclosure.

Referring to FIG. 5, an example image capture system 500 that may be used to generate annotated infrared images as described herein will now be described, in accordance with one or more embodiments. In the illustrated embodi-ment, the image capture system is configured to capture and process both visible and infrared images, align the pair of captured images, and annotate the infrared image and/or visible image for use in training an image classifier for a variety of uses. In some embodiments, the image capture system 500 is configured to operate as described with respect to the embodiment of FIG. 3.

The image capture system 500 may be used for imaging a scene 570 in a field of view. The image capture system 500 includes a processing component 510, a memory component 520, an infrared camera 501a, a visible-light camera 501b, an optional display component 540, a control component 550, a communication component 552, and other compo-nents depending on the system implementation. The infrared camera 501a includes IR image optical components 532a (e.g., one or more lenses configured to receive radiation through an aperture 534a in infrared camera 501a and pass the radiation to IR image capture component 530a), IR image capture components 530a, and an IR image capture interface component 536a.

IR image capture components 530a include, in one embodiment, one or more sensors for capturing infrared image signals representative of an image, of scene 570. The sensors of image capture components 530a provide for representing (e.g., converting) a captured infrared image signal of scene 570 as digital data (e.g., via an analog-todigital converter included as part of the sensor or separate from the sensor as part of image capture system 500). In some embodiments, the image capture components 530*a* include infrared sensors (e.g., infrared detectors) implemented in an array or other fashion on a substrate. For example, infrared sensors may be implemented as a focal plane array (FPA). Infrared sensors may be configured to detect infrared radiation (e.g., infrared energy) from a target scene including, for example, midwave infrared wave bands (MWIR), longwave infrared wave bands (LWIR), and/or other thermal imaging bands as may be desired. Infrared sensors may be implemented, for example, as microbolometers or other types of thermal imaging infrared sensors arranged in any desired array pattern to provide a plurality of pixels. In some embodiments, the infrared camera 501*a* may include a 3-5 micron high-definition MWIR camera (e.g., capturing infrared images at 1344×784 pixels).

The visible-light camera 501*b* includes visible image optical components 532*b* (e.g., one or more lenses configured to receive visible spectrum radiation through an aperture 534*b* in camera 501*b* and pass the received visible spectrum to visible image capture component 530*b*), visible image capture components 530*b*, and a visible image capture interface component 536*b*. Visible image capture components 530*b* include, in one embodiment, one or more sensors for capturing visible-light image signals representative of an image of scene 570. The sensors of visible image capture components 530*b* provide for representing (e.g., converting) a captured visible-light image signal of scene 570 as digital data (e.g., via an analog-to-digital converter included as part of the sensor or separate from the sensor as part of image capture system 500). In some embodiments, the visible image capture components 530*b* include light sensors implemented in an array or other fashion on a substrate. For example, sensors may be implemented as a charge-coupled-device (CCD) sensor, scientific complementary metal oxide semiconductor (sCMOS) sensor, or other visible-light sensor.

In various embodiments, image capture system 500 may be implemented as a paired imaging system to simultaneously capture image frames of the scene 570 using IR camera 501*a* and visible-light camera 501*b*. In various embodiments, the cameras 501*a* and 501*b* may represent any type of camera system that is adapted to image the scene 570 and provide associated image data as described herein. The image capture system 500 may be implemented at various types of fixed locations and environments, or in a portable device or vehicle. The system includes a beamsplitter 502 which separates visible and infrared radiation from the scene 570. The visible-light camera 501*b* and the infrared camera 501*a* are positioned to receive the separated visible and infrared radiation, respectively. The infrared camera 501*a* (e.g., a midwave IR camera) is mounted to capture a reflection of the scene folded through a 90-degree angle by the beamsplitter 502 which is viewed by the infrared camera 501*a* at a 45-degree angle. The visible-light camera 501*b* is mounted to capture a visible-light image of the scene 50 through the beamsplitter 502. In various embodiments, it is desirable for the optical axes of the visible-light camera 501*b* and the infrared camera 501*a* to be precisely lined up so that there is negligible perspective change between the two captured images, which allows for the creation of accurately registered images at various distances.

The optical components 532*a* and 532*b* for the two cameras may be selected to match the fields of view between the cameras, and/or adjustments to the captured images (e.g., cropping the larger image) may be performed after image capture. In some embodiments, the cameras are mounted on a board and can be adjusted in elevation and azimuth angles. Precision spacers underneath the mounts or other mounting components may be used to set the height of the optical axes to the same heights. A glare stop 504, such as a piece of dark grey foam, is positioned adjacent to the beamsplitter 502 to reduce reflections of visible-light off the side of the beamsplitter 502 facing the visible-light camera 501*b*.

The beamsplitter 502 may be implemented as a dichroic beamsplitter made of 0.3" BK7 glass, with one side of the glass coated with a layer of indium tin oxide (ITO) which makes it ~80% reflective in the midwave IR band (3-5 microns in wavelength units). In this embodiment, the beamsplitter 502 may be ~90% transparent to visible-light. In various embodiments, the beamsplitter 502 may be any beamsplitter that reflects a desired infrared band and is transparent to visible-light to allow for high quality image capture.

Processing component 510 may include, for example, a microprocessor, a single-core processor, a multi-core processor, a microcontroller, a logic device (e.g., a programmable logic device configured to perform processing operations), a digital signal processing (DSP) device, one or more memories for storing executable instructions (e.g., software, firmware, or other instructions), a graphics processing unit and/or any other appropriate combination of processing device and/or memory to execute instructions to perform any of the various operations described herein. Processing component 510 is adapted to interface and communicate with components 536*a*, 536*b*, 520, 530, 540, and 550 to perform methods and processing steps as described herein. Processing component 510 may also be adapted to perform synchronization 580 of the cameras 501*a* and 501*b* to capture images of the scene 570 at approximately the same time and with approximately the same integration period, image processing through image processing component 582, and/or image pair registration (image pair registration component 584) as described herein.

It should be appreciated that processing operations and/or instructions may be integrated in software and/or hardware as part of processing component 510, or code (e.g., software or configuration data) which may be stored in memory component 520. Embodiments of processing operations and/or instructions disclosed herein may be stored by a machine-readable medium in a non-transitory manner (e.g., a memory, a hard drive, a compact disk, a digital video disk, or a flash memory) to be executed by one or more computers (e.g., logic or processor-based system) to perform various methods disclosed herein.

Memory component 520 includes, in one embodiment, one or more memory devices (e.g., one or more memories) to store data and information. The one or more memory devices may include various types of memory including volatile and non-volatile memory devices, such as RAM (Random Access Memory), ROM (Read-Only Memory), EEPROM (Electrically-Erasable Read-Only Memory), flash memory, or other types of memory. In one embodiment, processing component 510 is adapted to execute software stored in memory component 520 and/or a machine-readable medium to perform various methods, processes, and operations in a manner as described herein.

Processing component 510 may be adapted to receive image signals from image capture components 530*a* and 530*b*, process image signals (e.g., to provide processed image data), store image signals or image data in memory component 520, and/or retrieve stored image signals from memory component 520. In various aspects, processing component 510 may be remotely positioned, and processing component 510 may be adapted to remotely receive image signals from image capture components 530 via wired or wireless communication with image capture interface component 536, as described herein.

Display component 540 may include an image display device (e.g., a liquid crystal display (LCD)) or various other types of generally known video displays or monitors. Control component 550 may include, in various embodiments, a user input and/or interface device, such as a keyboard, a control panel unit, a graphical user interface, or other user input/output. Control component 550 may be adapted to be integrated as part of display component 540 to operate as both a user input device and a display device, such as, for example, a touch screen device adapted to receive input signals from a user touching different parts of the display screen.

Processing component 510 may be adapted to communicate with image capture interface components 536a and 536b (e.g., by receiving data and information from image capture components 530a and 530b). Image capture interface components 536a and 536b may be configured to receive image signals (e.g., image frames) from image capture components 530a and 530b, respectively, and communicate image signals to processing component 510 directly or through one or more wired or wireless communication components (e.g., represented by connection 537) in the manner of communication component 552.

In one or more embodiments, communication component 552 may be implemented as a network interface component adapted for communication with a network and may include one or more wired or wireless communication components. In various embodiments, a network may be implemented as a single network or a combination of multiple networks, and may include a wired or wireless network, including a wireless local area network, a wide area network, the Internet, a cloud network service, and/or other appropriate types of communication networks. The image capture system 500 may be configured to operate with one or more computing devices, servers and/or one or more databases, and may be combined with other components. In some embodiments, image capture system 500 may send image pairs over a network (e.g., the Internet or the cloud) to a server system, for remote image pair registrations and processing, annotations, and other processes as disclosed herein.

Registered image pairs may be provided to an annotation system 556 for further processing. In various embodiments, the annotation system 556 may be integrated into a local computing system with one or more other components of image capture system 500, accessed through a wireless or wired communications link, accessed through a network, such as the Internet or a cloud service, a standalone system (e.g., receiving registered image pairs via an external memory device), a mobile system, or other system configured to perform the systems and methods described herein. In various embodiments, the annotation system 556 includes infrared classification components 557 for automatically (e.g., using a trained CNN) and/or manually (e.g., user interface) analyzing infrared images and visible classification components 558 for automatically and/or manually analyzing visible images. The image classification may include, for example, detecting one or more objects in an image, defining a bounding box around detected objects, and/or classifying detected objects. The annotation components 559 are configured to provide an interface that synthesizes the infrared and visible classification information for an image pair allowing a user to view the images and proposed annotations and confirm and/or edit the annotations. The annotated image pairs may then be stored in a database 560 for use in training and/or validating a neural network for infrared image classification.

Various aspects of the present disclosure may be implemented for training neural networks and/or other machine learning processes to analyze and/or classify captured infrared images for a variety of applications, including surveillance, traffic monitoring, detection and tracking of people, fever monitoring, etc. Embodiments of neural networking training systems and methods that may be used in the present disclosure will now be described with reference to FIGS. 6A-D.

Figures 6A, 6B:
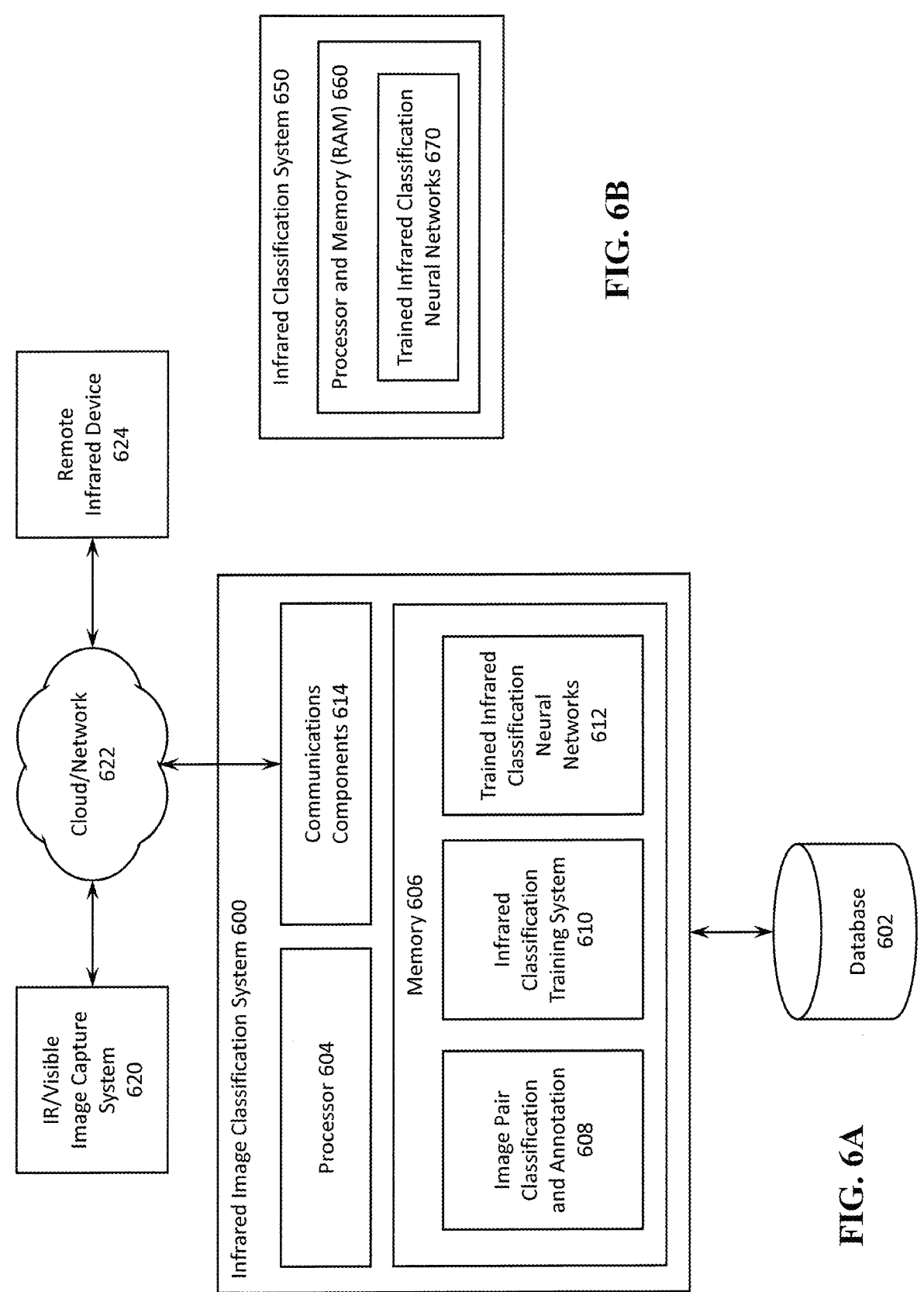
FIG. 6A illustrates an infrared classification training system, in accordance with one or more embodiments.
FIG. 6B illustrates an infrared classification system, in accordance with one or more embodiments.

Referring to FIG. 6A, embodiments of an infrared classification system will be described. The infrared classification system 600 may be implemented as a standalone system and/or on one or more servers such as an application server that performs data processing and/or other software execution operations for training, storing, and neural networks used by the infrared classification system 600. In some embodiments, the components of the infrared classification system 600 may be distributed across a communications network, such as cloud/network 622. The communications network 622 may include one or more local networks such as a wireless local area network (WLAN), wide area networks such as the Internet or cloud network, and other wired or wireless communications paths suitable for facilitating communications between components as described herein. The infrared classification system 600 includes communications components 614 operable to facilitate communications with one or more remote systems, such as a remote infrared device 624 configured to capture one or more infrared images of a scene and detect and/or classify objects therein, and an infrared/visible image capture system 620 configured to capture registered infrared/visible image pairs for use in training an infrared image classification system.

In various embodiments, the infrared classification system 600 may operate as a networked infrared image classification system, such as a cloud-based system, or may be configured to operate in a dedicated system, such as a surveillance system that processes thermal images and other data captured in real time from one or more surveillance devices (e.g., a thermal imaging camera as described herein). The infrared classification system 600 may be configured to analyze the captured data and return information relating to an infrared image classification, such as location of detection objects, classification of detected objects, confidence measure for the classification, etc. The infrared classification system 600 may also include a database 602 for storing captured infrared/visible image pairs, training datasets, trained neural networks, and other information.

As illustrated, the infrared classification system 600 includes one or more processors 604 that perform data processing and/or other software execution operations. The processor 604 may include logic devices, microcontrollers, processors, application specific integrated circuits (ASICs), field programmable gate arrays (FPGAs) or other devices that may be used by the infrared image classification system 600 to execute appropriate instructions, such as software instructions stored in memory 606 including image pair classification and annotation components 608, infrared classification training system components 610, trained infrared classification neural networks 612 (e.g., a convolutional neural network trained by a training dataset stored in the database 602), and/or other applications.

The memory 606 may be implemented in one or more memory devices (e.g., memory components) that store executable instructions, data and information, including image data, video data, audio data, network information. The memory devices may include various types of memory for information storage including volatile and non-volatile memory devices, such as RAM (Random Access Memory), ROM (Read-Only Memory), EEPROM (Electrically-Erasable Read-Only Memory), flash memory, a disk drive, and other types of memory described herein.

The remote infrared device 624 may be implemented as a computing device such as a thermal imaging camera, a handheld temperature sensing device, a desktop computer or network server, a mobile computing device such as a mobile phone, tablet, laptop computer or other computing device having communications circuitry (e.g., wireless communications circuitry or wired communications circuitry) for connecting with other devices. In some embodiments, the remote infrared device 624 may include one or more unmanned vehicles (e.g., drones) such as an unmanned aerial vehicle, an unmanned ground vehicle, or other unmanned vehicle.

The communications components 614 may include circuitry for communicating with other devices using various communications protocols. In various embodiments, communications components 614 may be configured to communicate over a wired communication link (e.g., through a network router, switch, hub, or other network devices) for wired communication purposes. For example, a wired link may be implemented with a power-line cable, a coaxial cable, a fiber-optic cable, or other appropriate cables or wires that support corresponding wired network technologies. Communications components 614 may be further configured to interface with a wired network and/or device via a wired communication component such as an Ethernet interface, a power-line modem, a Digital Subscriber Line (DSL) modem, a Public Switched Telephone Network (PSTN) modem, a cable modem, and/or other appropriate components for wired communication. Proprietary wired communication protocols and interfaces may also be supported by communications components 614.

One or more trained infrared classification systems may be implemented in a remote, real-time environment, as illustrated in FIG. 6B. The infrared classification system 650 may include a thermal imaging camera or other device or system operable to receive and/or generate thermal images and process the received thermal images for input to a trained infrared classification neural network 670. The infrared classification system 650 includes a processor and memory 660, operable to store one or more trained neural networks and implement the neural network run-time interface (such as trained infrared classification neural network 670) thereon.

Figures 6C, 6D:
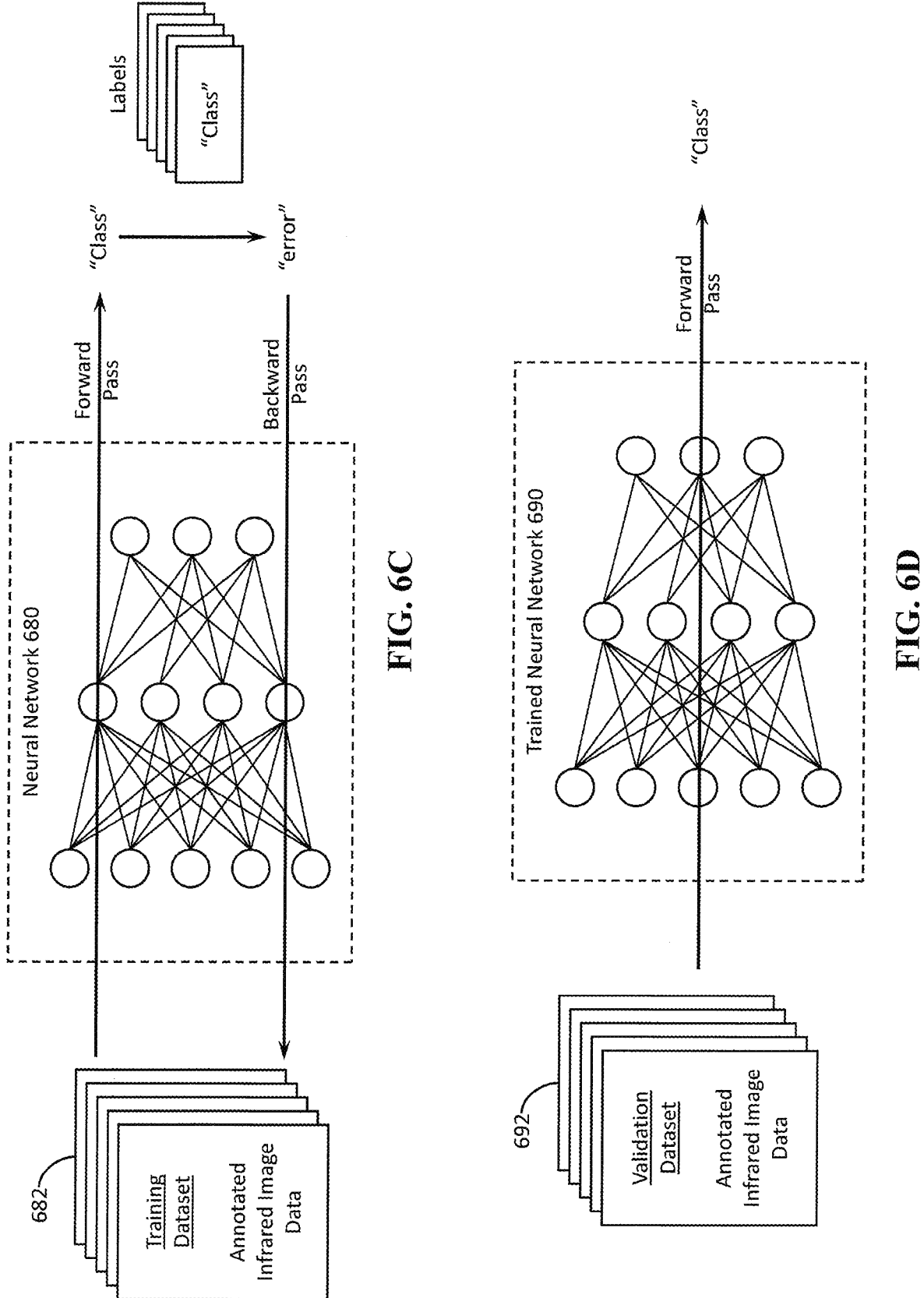
FIGS. 6C and 6D illustrate neural network training and validation processes, in accordance with one or more embodiments.

In various embodiments, a training dataset stored in the database 602 may be created from annotated registered image pairs and used to train one or more neural networks and other machine learning algorithms for use in an infrared classification system. Referring to FIG. 6C, an embodiment of a neural network training process will now be described. In one embodiment, the neural network 680 is a convolutional neural network (CNN) that receives the training dataset 682 and outputs a classification for the data. The present disclosure describes a plurality of neural networks that may be trained for one or more infrared image determinations, including but not limited to, detecting and tracking objects and/or people from thermal images, detection of a temperature measurement location in a thermal image, classification of a detected object, and/or determination of whether an individual has a fever.

The training dataset includes annotated infrared image data created from registered visual and infrared pairs as described herein. The data may also include annotated infrared data created through other means, including synthetic data generated to simulate real-world images. In one embodiment, the training starts with a forward pass through the neural network 680 including feature extraction, a plurality of convolution layers and pooling layers, a plurality of fully connected layers, and an output layer that includes the desired classification. Next, a backward pass through the neural network 680 may be used to update the CNN parameters in view of errors produced in the forward pass (e.g., misclassified data). In various embodiments, other processes may be used in accordance with the present disclosure.

An embodiment for validating the trained neural network is illustrated in FIG. 6D. A set of fully annotated validation test data 692 is fed into the trained neural network 690. The validation test data 692 may include annotated infrared data generated from registered infrared/visible image pairs as described herein, that was not used as part of the training dataset 682. Detected errors (e.g., image misclassification) may be analyzed and fed back to the training system to update the training model, which in turn updates the training dataset 682 to create a more accurate classification model. In various embodiments, detected errors may be corrected by adding more examples of the data (e.g., more types of environments), increasing the resolution of the data and/or increasing the accuracy of the thermal modeling, to help distinguish between data types. By adjusting the training dataset to improve accuracy on-the-fly, the operator can avoid costly delays in implementing accurate classification systems.

In various embodiments, the system is configured to save data generated in real-time in the field for analysis and training of one or more neural networks. For example, data from a deployed system may be fed back into a CNN training process to refine the CNN to improve classification for a particular environment (e.g., detect temperature of people in an airport), desired classification goal (e.g., train the CNN to detect and track one or more objects) and/or for more accurate performance.

Dual-Band Temperature Detection Systems and Methods

The various training processes disclosed herein may be used to train infrared imaging systems for a variety of detection and classification tasks. In some embodiments, systems for measuring elevated body temperature (EBT) make use of thermal infrared cameras to measure skin temperature without physical contact—an important aspect of any system used in the presence of people with potentially infectious diseases. A person with a fever will have an elevated core body temperature and under certain conditions, this elevated temperature can manifest itself through skin temperature, particularly on facial skin near the tear duct (canthus), an area of the face with a high degree of blood flow. This canthus surface temperature may only be a few degrees C. cooler than the core body temperature.

Figure 7:
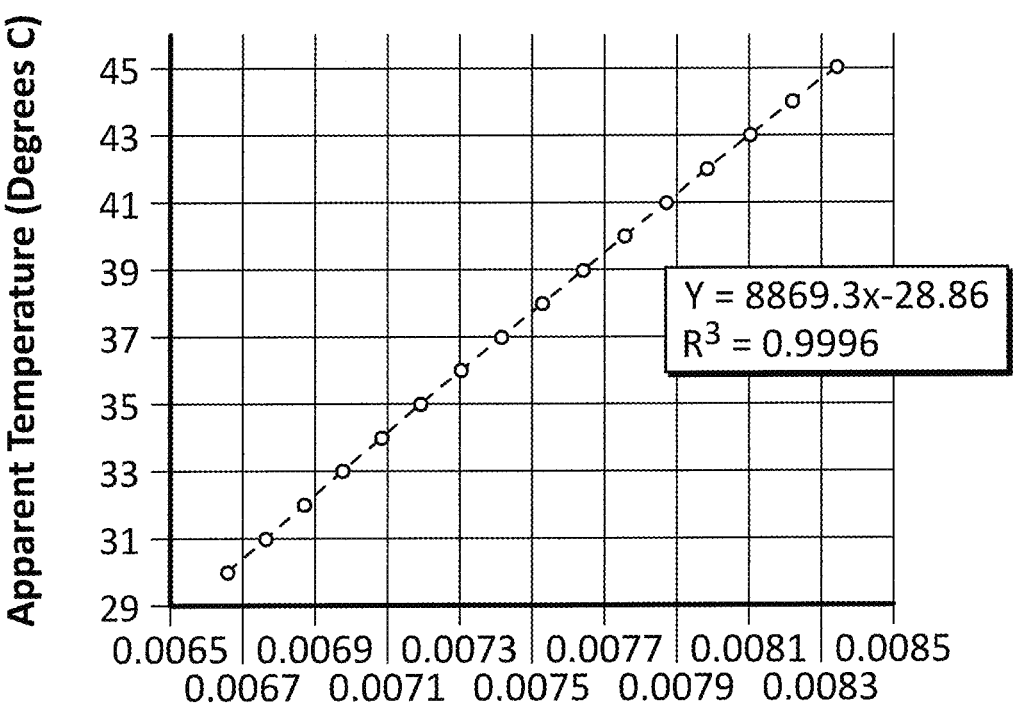
FIG. 7 illustrates a relationship between blackbody temperature and in-band radiance, in accordance with one or more embodiments.

The thermal infrared camera is calibrated to accurately measure the difference between a healthy person and a febrile person may only be a matter of a few degrees C. difference in core body temperature. The standard calibration of an infrared camera relates the digital counts for each pixel in the image to the radiance of a surface viewed by those pixels (in the spectral band of the thermal camera). The temperature of the surface can be derived from the radiance measured by the camera by various methods, including a lookup table. In the case of skin temperature measurements, it is possible to calibrate the system directly from digital counts to temperature for two reasons. The first reason is that the range of facial skin temperatures is limited to values from 30° C. to ~38° C. Over this range of temperature, the in-band radiance for a 7-14 micron longwave camera is nearly linear in temperature, as shown in FIG. 7.

Figures 8A, 8B:
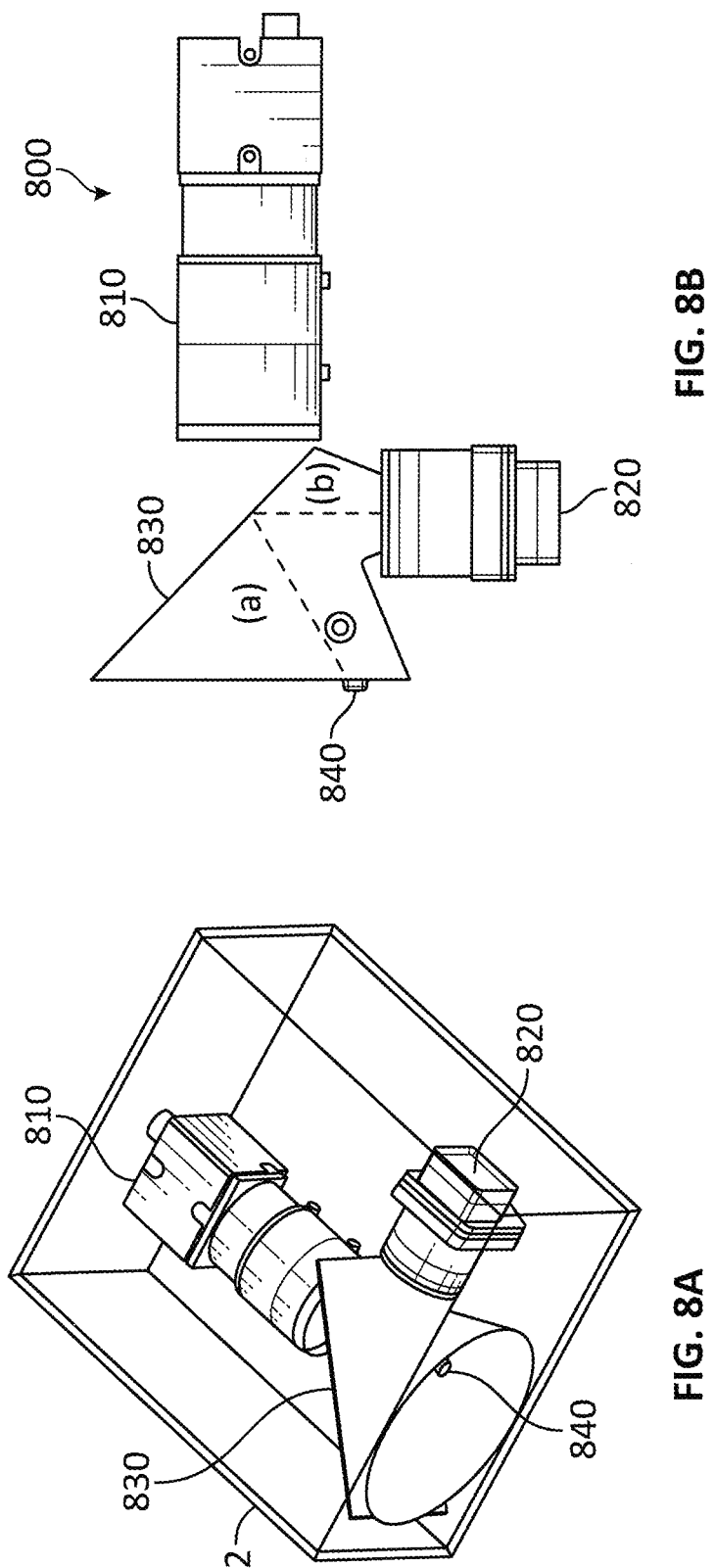
FIGS. 8A and 8B illustrate a dual-band image capture system in accordance with one or more embodiments.

Referring to FIGS. 8A and 8B, an example embodiment of a trained dual-band imaging system will be described, in accordance with one or more embodiments. A dual-band camera 800 includes a first camera 810, a second camera 820, and a beamsplitter 830. The first camera 810 includes image capture and processing components configured to sense and capture a visible image of a field of view. The second camera 820 includes image capture and processing components configured to sense and capture an infrared image of the field of view. The first camera 810 and the second camera 820 are arranged in a camera body 802 and configured to capture the images through a beamsplitter 830 at substantially the same time. The beamsplitter 830 reflects an image of the scene to the second camera 820, while the first camera 810 captures the visible images through the beamsplitter 830. The arrangement disclosed herein allows image pairs to be captured with minimal parallax, which facilitates accurate image processing and classification as described herein.

In some systems, a blackbody 840 may be present in the field of view. In some embodiments, the blackbody may be positioned as part of the dual-band camera 800 and/or positioned closed to the camera body 820. The reflection of the blackbody 840 radiation off the beamsplitter 830 allows the black body to positioned physically closer to the thermal camera due to the folded geometry (e.g., black body 840 is (a)+(b) away from the thermal camera 820). In some embodiments, placing blackbody close to the thermal camera allows the black body to appear larger to the thermal camera, and also allows for precision placement of the blackbody at a location to be captured by the thermal camera 820, but outside of the usable image. In various embodiments, the blackbody may include a thermistor, a micro-cavity blackbody (e.g., a long, tapered cone) or other blackbodies. For example, a thermistor, a calibrated device with a resistance value as a function of temperature, can be used as a blackbody by heating the thermistor by passing a current through it, measuring the resistance to get the temperature, which can then be compared to a sensed blackbody temperature from a thermal image.

Additional aspect of the present disclosure will now be described with reference to FIG. 9. The skin on a person's face has an in-band emissivity that is very close to the typical emissivity of an area blackbody source, e.g., 0.96. The digital counts measured by an infrared camera looking at a blackbody source and human skin will be the same if the two surface temperatures are the same. An EBT system may have a reference blackbody (or blackbodies) in the field of view at all times, which has the property of embedding a temperature calibration into every thermal infrared image. This also makes it possible to use cameras that do not have built-in calibrations, which may be lower cost to produce because the camera does not require a time-consuming radiometric calibration process. An additional advantage is that atmospheric transmission is folded into the in-scene calibration if the blackbody is located at the same distance from the camera as the test subject.

Figure 9:
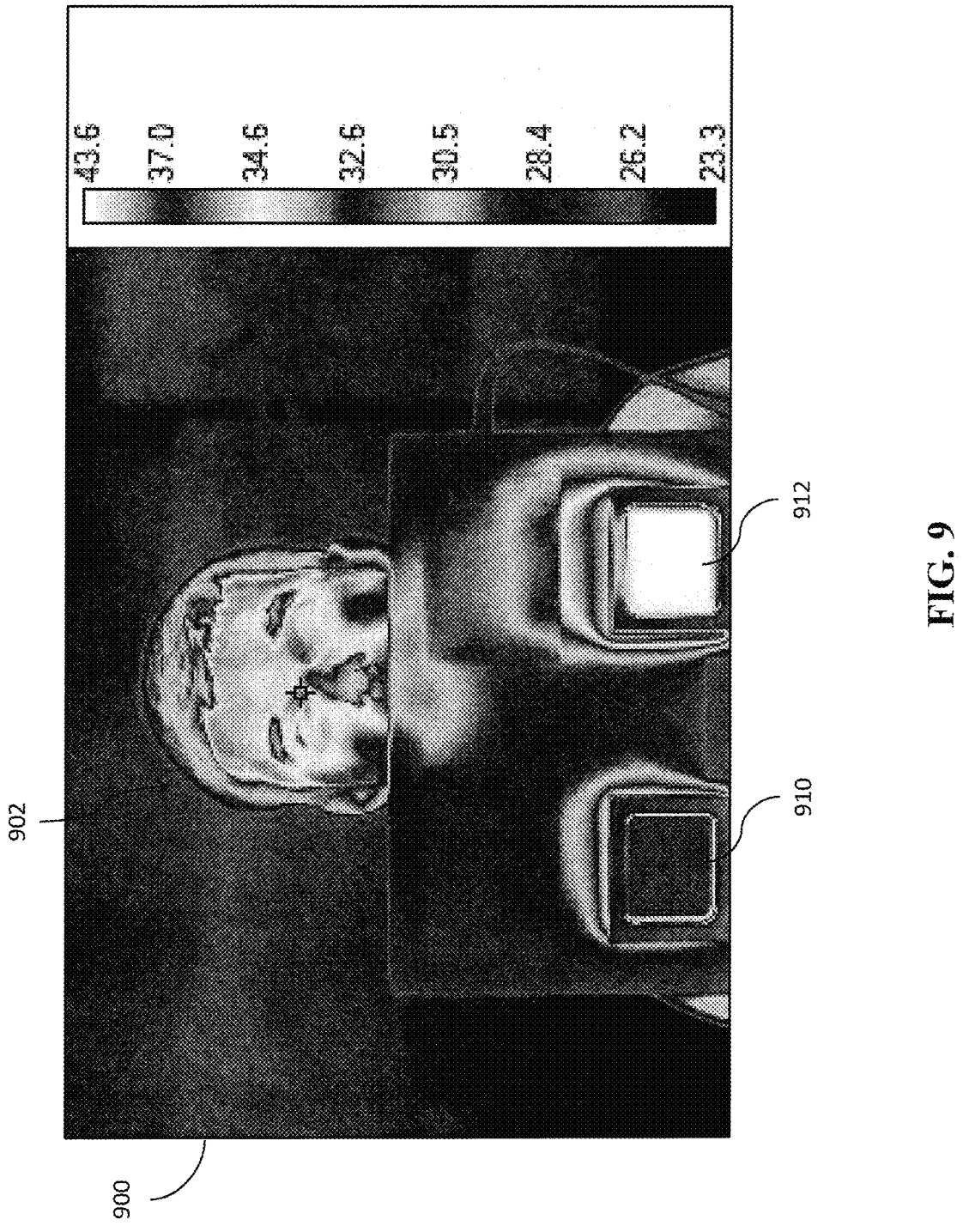
FIG. 9 illustrates a thermal image with a test subject and two blackbodies, in accordance with one or more embodiments.

FIG. 9 illustrates a thermal image 900 of a test subject 902 with a dual blackbody system in the field of view. A first blackbody 910 has a temperature of 35 C, and a second blackbody 912 has a temperature of 41 C. Temperatures can be interpolated and extrapolated from the digital count values on the two blackbodies, or on a single blackbody if the responsivity of the camera is known. In the case of the single blackbody configuration, it may be necessary to know the responsivity of the camera.

Referring to FIG. 10, a method 1000 to measure temperature using a single reference blackbody will now be described in accordance with one or more embodiments. In step 1010, the responsivity of the camera is measured using two blackbodies (e.g., at 35 C and 40 C) with the camera fully warmed up and operating in an environment representative of an expected temperature of operation. The camera software may be configured to provide frame averaging to reduce temporal noise, and the responsivity may be calculated as the difference in digital counts on two regions of interest (ROIs) positioned on the two blackbodies (e.g., 571.8 counts), divided by the temperature difference, which in this example is 5° C. The resulting responsivity is 114 counts/° C.

In step 1020, a region of interest is identified on the reference blackbody in the field of view of the camera while viewing a scene of interest which contains test subjects, and the mean digital counts on the reference blackbody are determined. This value is the reference offset. In step 1030, the system measures the digital counts on the target of interest, which may include a region on the face of a test subject (e.g., the hottest part of the face, a specific target location on the face such as a the canthus). The software could automatically detect the person's face, then locate the hottest spot on the face (e.g., the canthus) and place a spotmeter with a 3×3 pixel size on the centroid of the hot spot to generate the EBT counts measurement. In some embodiments, a visible images is captured and used to identify the object and/or location on the object, and the identified location can then be measured at the corresponding location on the thermal image In step 1040, the reference offset is subtracted from the EBT counts measurement. The system then divides by the responsivity to get a relative temperature difference between the test subject's canthus and the reference blackbody. This temperature difference is then added to the blackbody temperature. The blackbody temperature could be read out continuously by the software to have an updated measurement. This measurement value could be inserted into the metadata of the thermal image.

In step 1050, at the same time, a visible-light image of the test subject is recorded which could be used to further analyze the scene (e.g., help identify the subject). Additional metadata could also be recorded, including the air temperature in the proximity of the measurement site, the relative humidity, the range to the person from the camera (perhaps measured by a stereo camera rig, LIDAR, RADAR or another method). This data could be of additional benefit to determine the atmospheric transmission loss between the camera and the subject, and to correct for the spot size effect, which is a phenomenon whereby small targets appear to be colder than their actual kinetic surface temperature due to stray light in the optics and the modulation transfer function (MTF) of the camera system.

Figure 11:
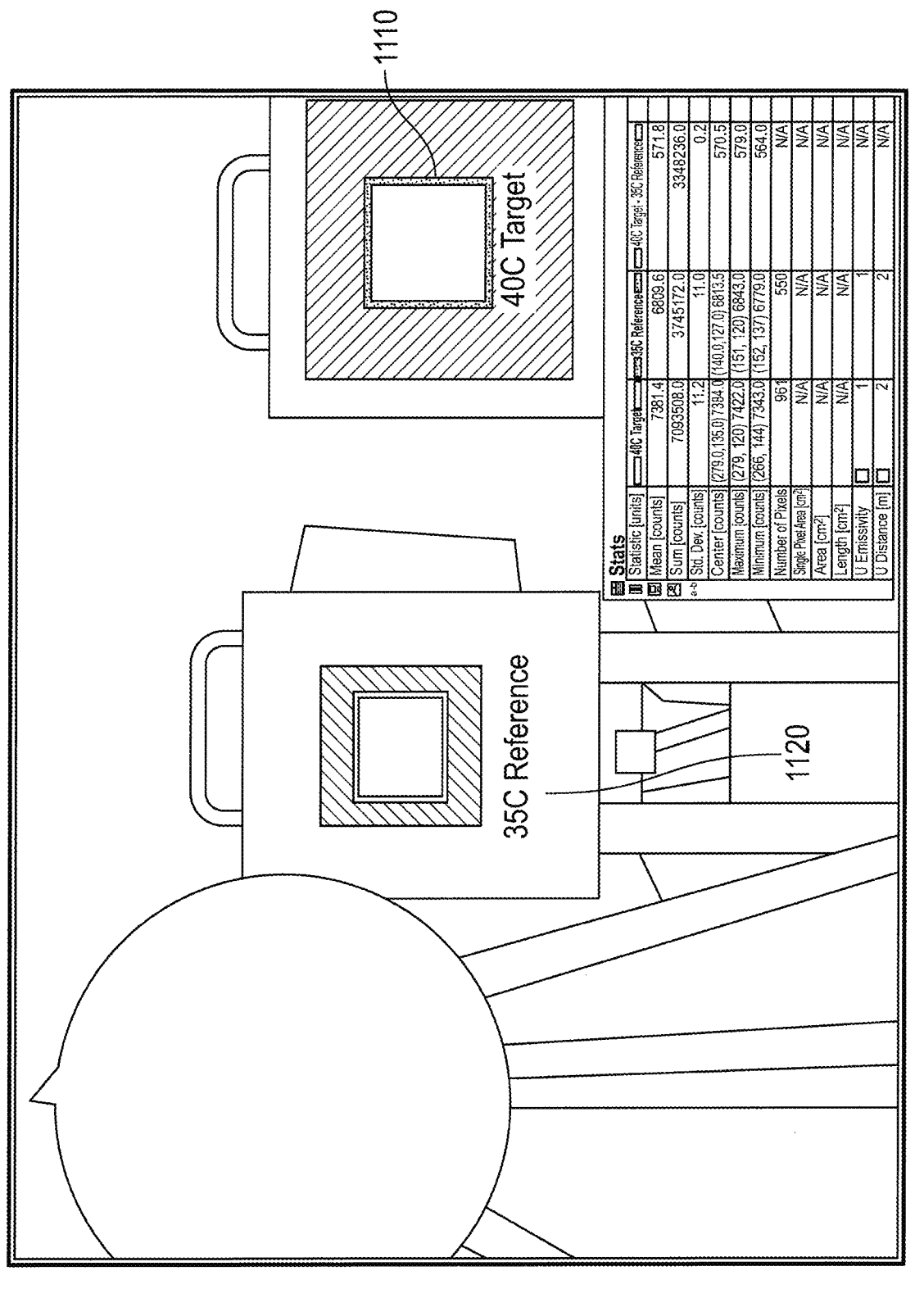
FIG. 11 is a figure illustrating a measurement of camera responsivity in ambient (23 C) operating conditions using two blackbodies.

Referring to FIG. 11, a measurement of camera responsivity will now be described, in accordance with one or more embodiments. A thermal image 1100 is captured by the infrared imaging camera of a field of view. The thermal image 1100 includes an image of a blackbody 1120, which has an associated region of interest (e.g., defined by green box labeled 35C Reference) in the thermal image 1100, from which temperature measurements are taken. A target 1110 is identified in the thermal image 1110 has an associated region of interest (e.g., defined by red box labeled 40C Target) from which temperature measurements for the target are taken.

Figure 12:
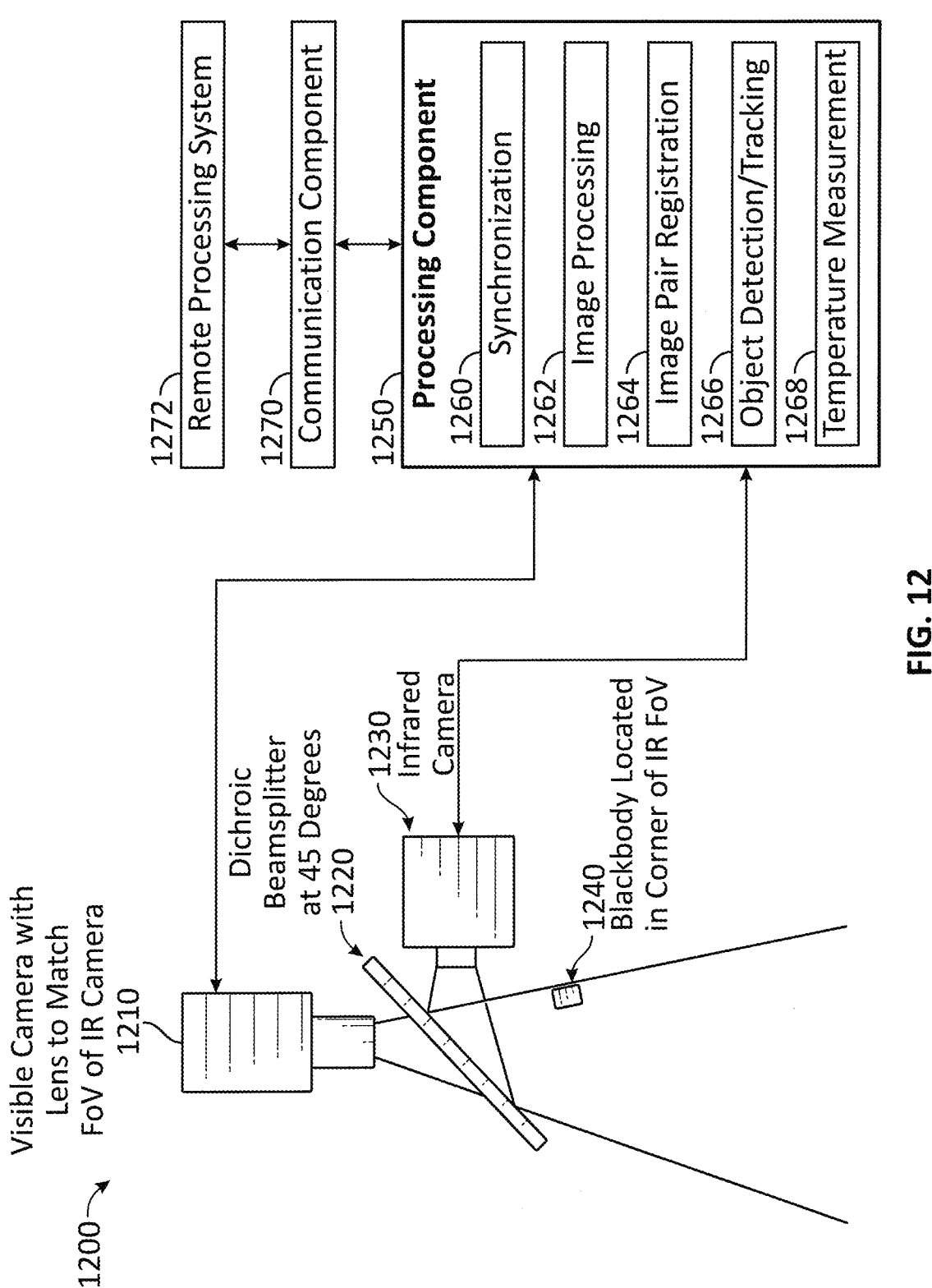
FIG. 12 is an example dual-camera system, in accordance with one or more embodiments.

Embodiments of example implementations of a dual-band camera will now be described with reference to FIG. 12. The dual-band camera 1200 is configured to reduce system parallax using a dichroic beamsplitter 1220. The dual-band camera 1200 may operate with a trained neural network that was trained using a dual-band camera system and beamsplitter as discussed herein. In the operation, the duel-band camera system 1200 captures video data from an infrared camera 1230 and video data from a visible camera 1210 simultaneously with the optical axes overlaid at a high level of precision. The dual-band camera 1200 uses the beamsplitter 1220 at a 45-degree angle relative to the optical axis of each camera (visible camera 1210 and infrared camera 1230). In various embodiments, the beamsplitter 1230 is coated with indium tin oxide on one side to reflect LWIR radiation with a ~90% efficiency to the infrared camera 1230, while simultaneously transmitting 90% of visible-light to the visible camera 1210. The illustrated system could be implemented in a variety of thermal imaging applications, including EBT applications because there is negligible parallax error between the visible and thermal IR images at all distances. In contrast, a conventional system with two side-by-side image sensors (e.g., boresighted visible and thermal IR cameras side-by-side) will result in a parallax error that becomes more noticeable at closer ranges, because the image pair cannot be registered perfectly in space for all object distances.

In some embodiments, a blackbody 1240 is located in a corner of the IR field of view (or other location that does not obstruct or minimally obstructs the captured image). For EBT applications, the dataset could be presented as a visible video of a target person where the system user could mouse over any point on the visible image and see the temperature on each point. This embodiment allows a system operator to intuitively explore different ways to view temperature in an EBT or other temperature measurement implementation. In some embodiments, the visible image may be discarded after object detection, analysis, and temperature measurement is performed to preserve the privacy of the subject (e.g., as may be required by law).

The dual-band camera 1200 is controlled by a processing component 1250 (e.g., such as one or more of the processing components of FIGS. 5-6B), configured in accordance with a particular use or implementation including synchronization logic 1260 for synchronizing the image capture of the two cameras (e.g., synchronizing shutters and image acquisition for temporal registration of captured images), image processing logic 1262 for processing the captured images into images for use by the system, image pair registration logic 1264 for aligning the image pair (e.g., pixel-by-pixel correspondence), object detection and tracking logic 1266 for identifying one or more target objects in the image pair, and temperature measurement logic 1268 for determining a temperature of an object or portion of an object. In various embodiments, one or more of the logical components may be implemented using image analysis, trained neural networks, statistical analysis, and/or other logic. In some embodiments, the dual-band camera 1200 communicates with a remote processing system 1272 through communications components 1270. The remote processing system

1272 may provide one or more services for the dual-band camera 1200 including training and downloading neural networks, online processing of image pairs, storage of historical data, and other services.

Figure 13:
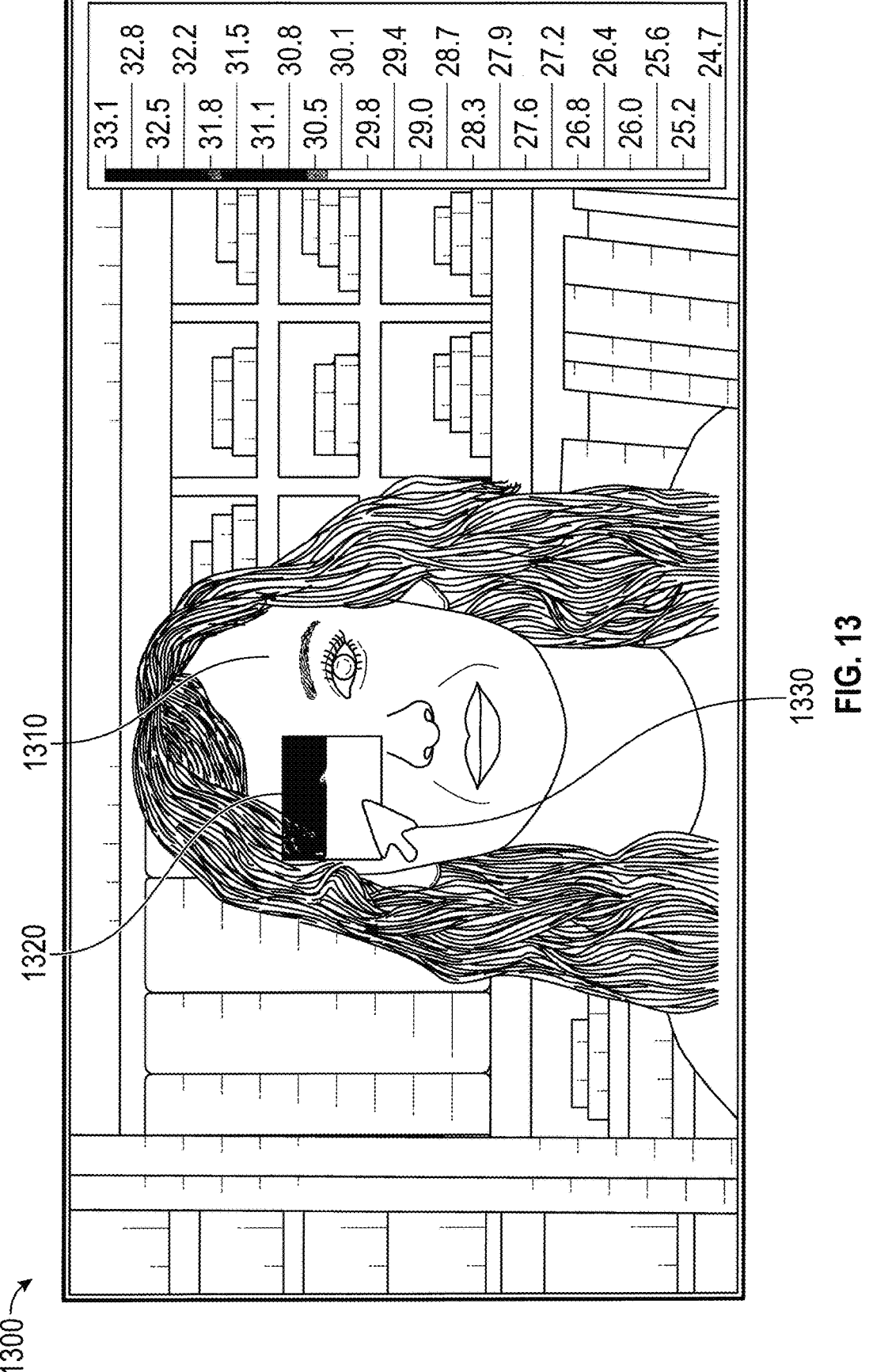
FIG. 13 is an example image captured with the dual-camera system of FIG. 12, in accordance with one or more embodiments.

An example of a method of displaying EBT data taken with the beamsplitter system is illustrated in FIG. 13. As illustrated, a display 1300 includes the visible image 1310 of an object (e.g., a person), which is overlaid with a thermal image inset 1320 on the visible image 1310 to show temperature data at a selected location (e.g., a location selected by the user by placing a pointer 1330 over a desired region). As illustrated, the hottest part of the test subject's face is the yellow portion on the canthus. The temperature is 33.1° C. as shown by the color bar on the right side.

Figure 14:
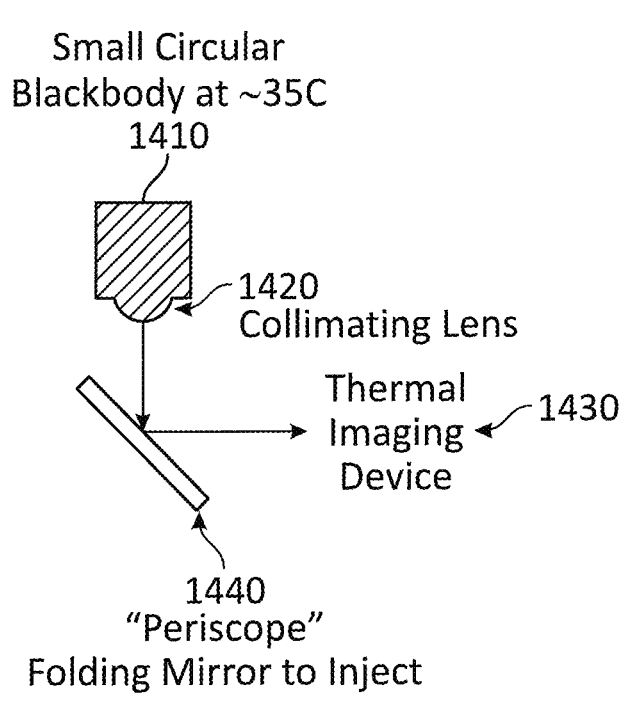
FIG. 14 illustrates an example arrangement of a blackbody in a dual-band imaging system, in accordance with one or more embodiments.

Referring to FIG. 14, the placement of the blackbody close to the IR camera will be in further detail, in accordance with one or more embodiments. The concept of placing a reference blackbody in the scene near the test subject or at the same distance as the test subject has the advantage that atmospheric transmission losses are "basked into" the calibration because both the test subject and the reference blackbody have their infrared signals changed by the same amount: reduced by the transmission of the air path, and increased by the air path signals themselves. However, placing the reference blackbody in the scene at distance has some distinct disadvantages. For one, the camera cannot be panned or tilted over the scene unless the reference blackbody is kept in the field of view and its location is known so that the software can maintain the positioning of an ROI on it. Another reason is that the reference blackbody may be bumped into, obscured by a person or other object or otherwise compromised since it is located in proximity to test subjects, a particularly undesirable situation when there is risk of cross-infection.

As illustrated, a system 1400 addresses these issues by placing a reference blackbody 1410 in the field of view of a thermal imaging device 1430 at a close distance to the camera lens. In some embodiments, the blackbody 1410 includes a small circular emitter made of aluminum coated with a high emissivity coating. A heating coil would be used to heat up the emitter and a thermistor or thermocouple could be used to monitor the absolute temperature of the emitter.

The blackbody 1410 will be highly out of focus if the blackbody is centimeters from the lens of the camera, while the lens is focused at some convenient working distance (e.g., 3 meters or some similar distance where everything in the scene from 1 meter to infinity would be in sufficient focus for measurement). If the blackbody 1410 is out of focus, then it will not be perceived as being at its actual physical temperature because it is a small target and the radiance from it will be smeared out over more pixels than if it was in focus. A solution to this problem is to place a collimating lens 1420 in front of the blackbody emitter 1410 to focus its rays so that the blackbody appears to be in focus.

A "periscope" folding mirror 1440 is provided to inject rays into the IR camera FoV.

In another embodiment, a shutter is periodically placed in front of the IR camera lens to expose the sensor to a known temperature scene. The shutter could be instrumented with temperature sensors which would then be used to calculate the reference offset. The shutter could also serve as the flat field correction shutter which would improve the spatial uniformity of the images. Putting the flat field correction shutter in front of the lens also corrects for the non-uniformity introduced by the lens assembly. The disadvantage of this approach is that temperature measurements of test subjects would not have the reference blackbody in the field of view at the same time, reducing traceability. There is also the matter of camera offset drift between activations of the reference shutter. This drift can be mitigated if the cameras are contained in a housing that has thermal mass enough to slow down any variations in ambient air temperature.

In various embodiments, systems and methods are provided for correcting for distance-induced temperature errors. The system is configured to correct the apparent temperature of a head based on its distance from the thermal imaging sensors so that someone who is sick does not get counted as healthy just because they are farther away from the camera. There are two effects that are at work to make the temperature measurement decrease with distance. One is atmospheric transmission. The other is the so-called "spot size effect". The spot size effect manifests itself as a decreasing apparent temperature of a target with decreasing angular size. It is observed that, with respect to the modulation transfer function of the optical system, as a hot target gets smaller, there is a "mixing" of cold pixels at the edges that begins to reduce the apparent temperature of the target. In some embodiments, the spot size effect is pronounced when the target is falls below a threshold size (e.g., is less than 15 by 15 pixels in size). The canthus hot spot on an adult is about 1 cm by 1 cm. It is observed that for an adult person's canthus to be at least 15×15 pixels in an image formed by an example camera having a 640×512 resolution with a 32-degree horizontal field of view, the target person should be less than 0.8 meters away.

For screening of people walking by in a crowd, it may be necessary to measure the distance from the camera to the heads of the targets, perhaps based on the size of the head (assuming adult heads). If we have visible-light images of the same scene, then trained artificial intelligence tools may be used to determine the ages and genders of people and then correct for their head sizes based on estimated age and gender. The distance measurement is used in an air path transmission model that accounts for target distance, air temp (e.g., using FPA temperature or external temperature sensor) and relative humidity (e.g., using a relative humidity sensor). In some embodiments, the air path transmission model is based on Moderate Resolution Atmospheric Transmission (MODTRAN), a radiative transport model developed by the Air Force.

Figure 15A:
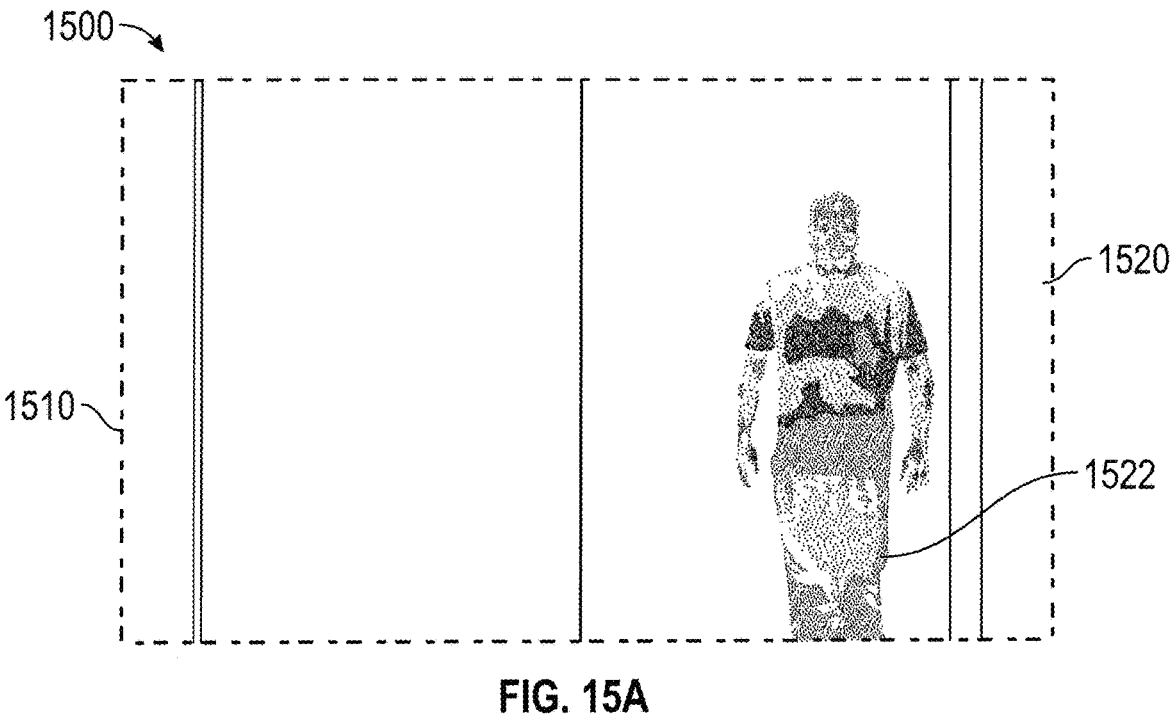
FIGS. 15A and 15B are example visible and infrared image pair, in accordance with one or more embodiments.
Figure 15B:
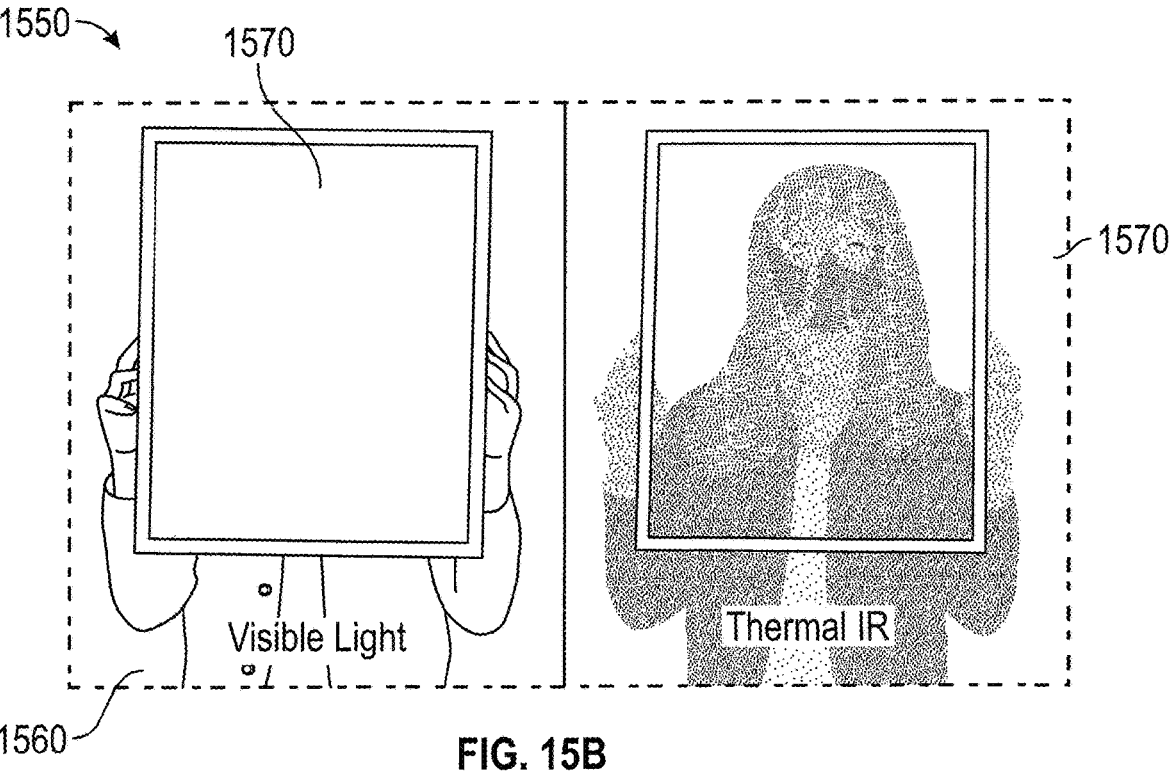

Referring to FIGS. 15A and 15B, examples of visible and infrared image pairs will now be described, in accordance with one or more embodiments. Image pair 1500 illustrates an example of a visible-light image 1510 showing fog and a thermal image 1520, showing an image of a man 1522 in the fog. Image pair 1550 illustrates an example of a visible-light image 1560 showing a person behind an obstruction 1570, and a corresponding thermal infrared image 1570. These examples illustrate benefits of a dual image camera system as described herein for both training and detection. Regarding training, the image pairs illustrate different contexts where labeling of visible and infrared images provide different context information for the scene. Object detection, tracking and classification can be improved using both visible-light images and infrared images, such as tracking an object when the visible-light image is obstructed.

Figure 16A:
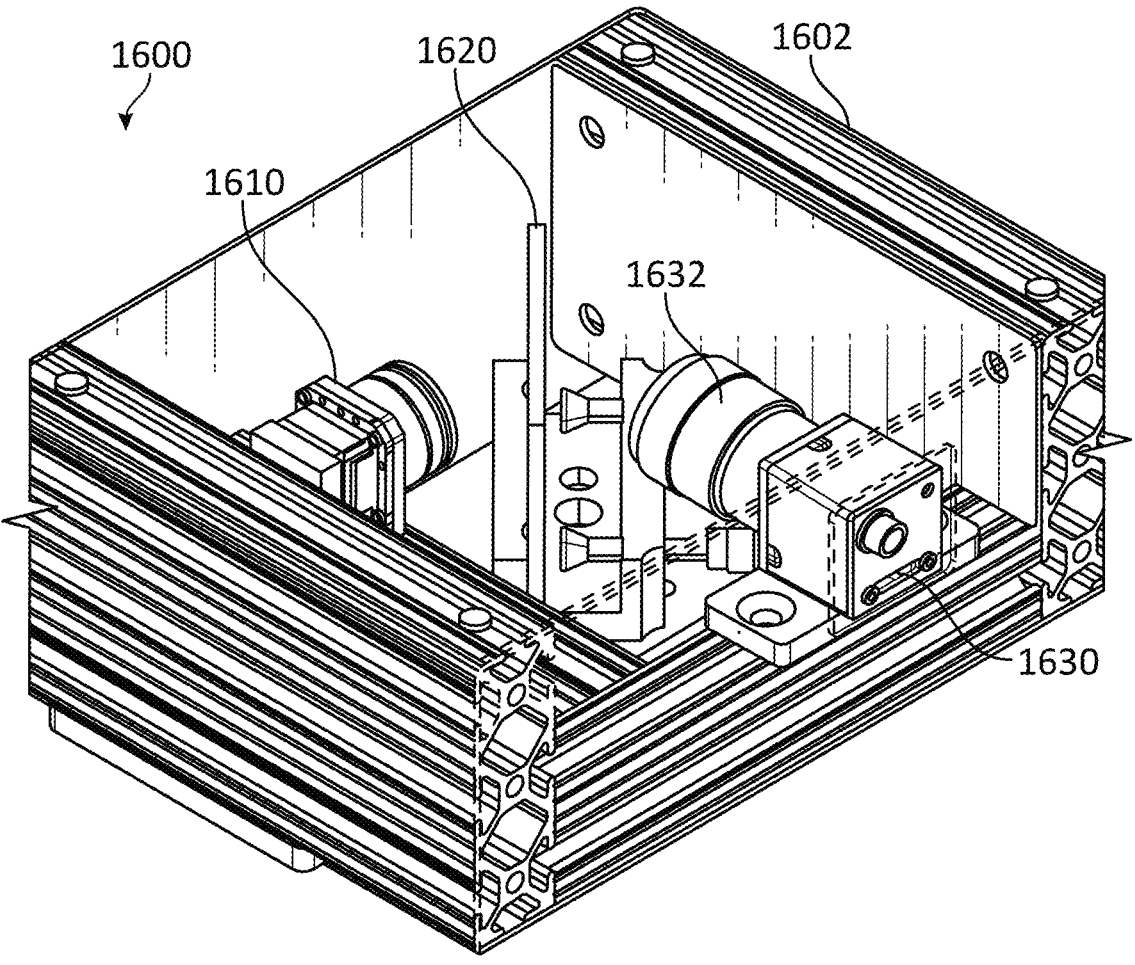
FIGS. 16A, 16B, 16C, and 16D are views of an example dual-band camera system, in accordance with one or more embodiments.
Figure 16B:
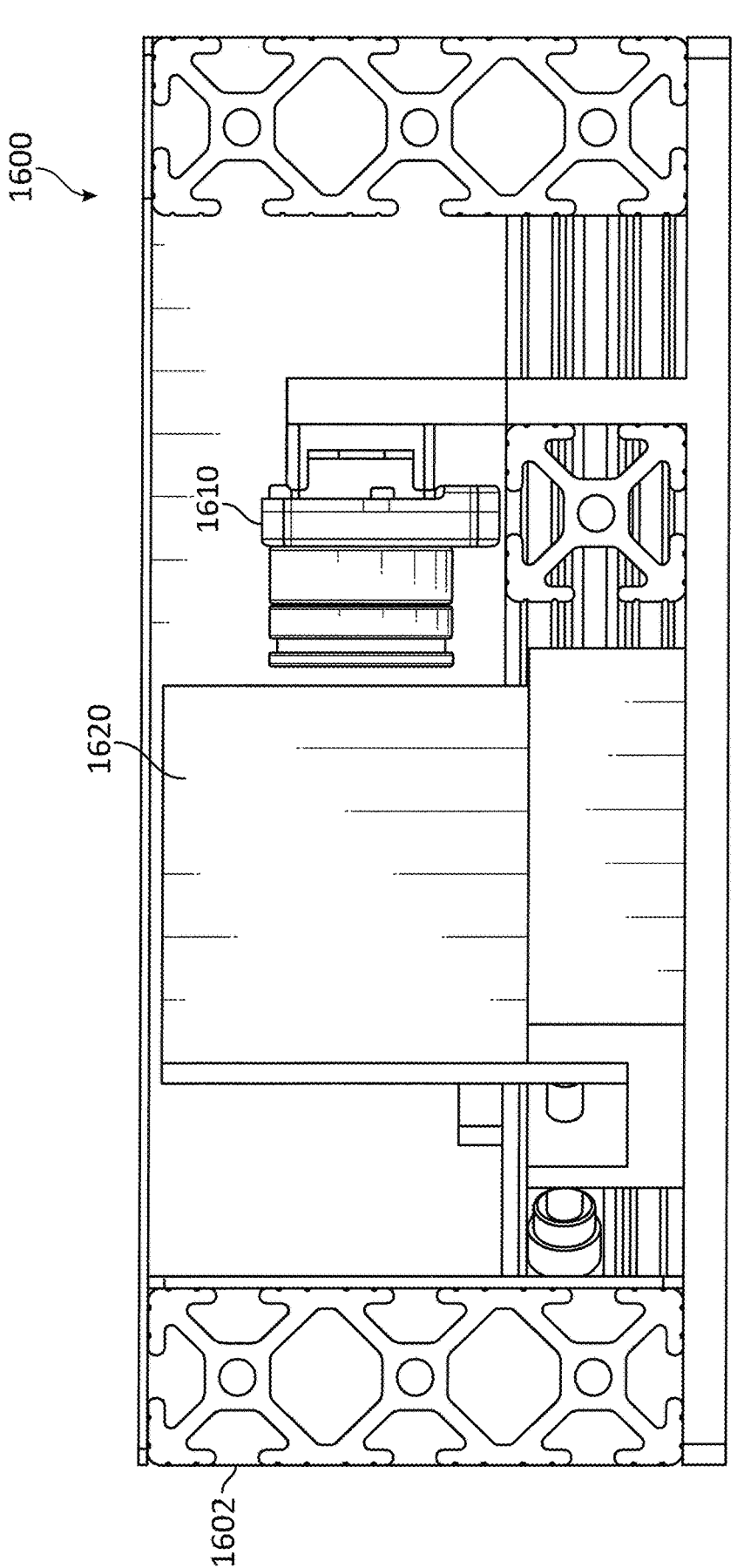
Figure 16C:
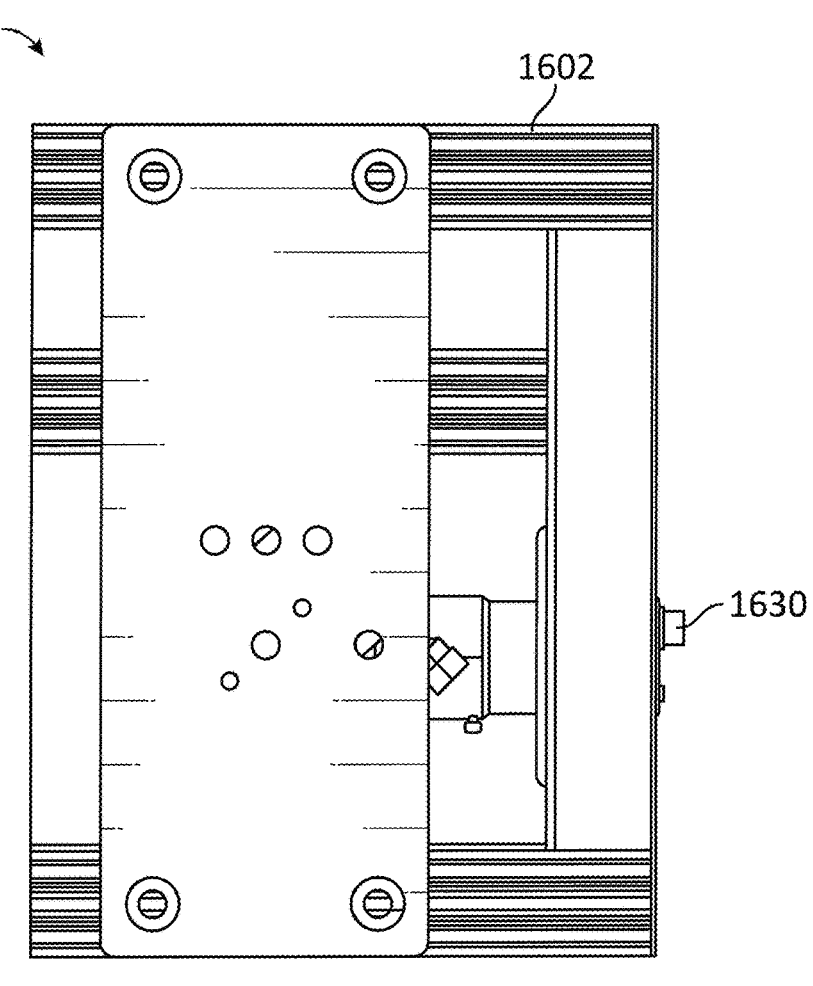
Figure 16D:
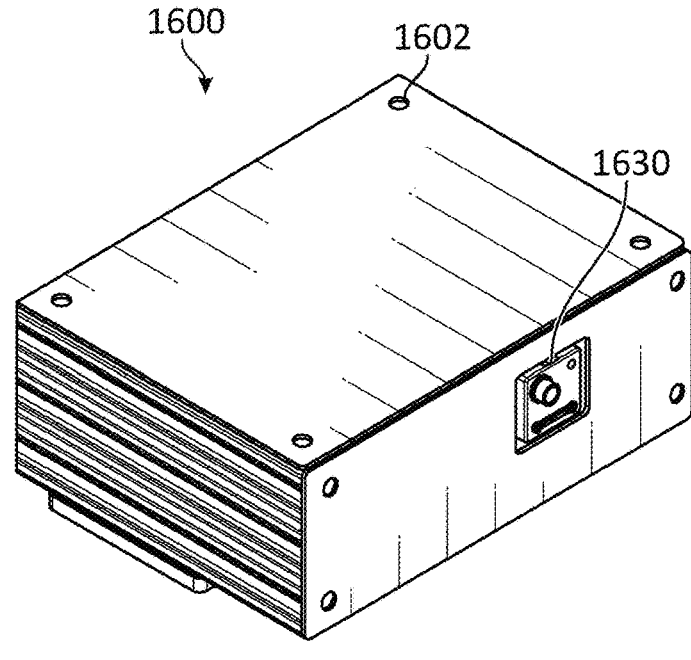

FIGS. 16A, 16B, 16C, and 16D are views of an example dual-band camera system, in accordance with one or more embodiments, including a perspective cutaway view (FIG. 16A), a side cutaway view (FIG. 16B), a bottom view (FIG. 16C), and a perspective view (FIG. 16D). An embodiment of a dual-band camera system 1600 includes a housing 1602, an infrared camera 1610, a beamsplitter 1620, a visible-light camera 1630 and optical components 1632 (e.g., a lens assembly) for focusing the visible-light image towards the image capture components of the visible-light camera 1630.

Figure 17A:
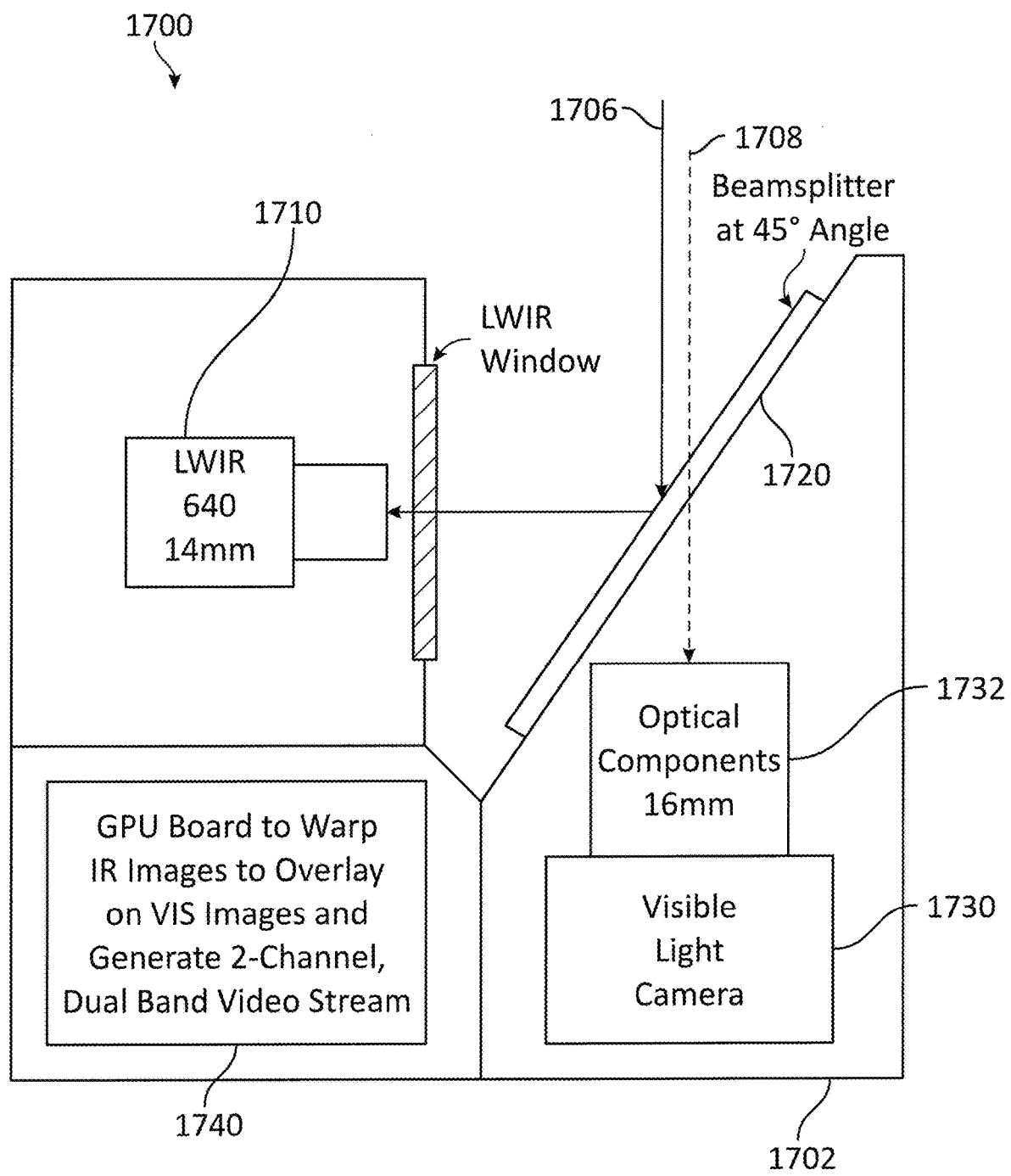
FIGS. 17A and 17B are views of another example dual-band camera system, in accordance with one or more embodiments.
Figure 17B:
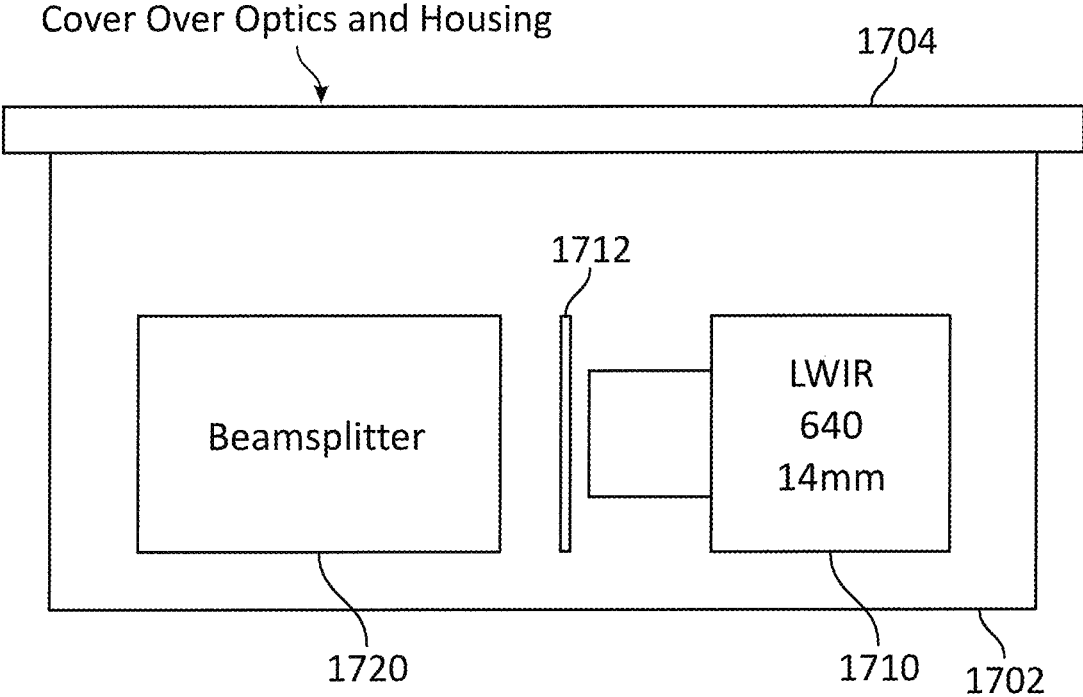

FIGS. 17A and 17B provide views of another example dual-band camera system, in accordance with one or more embodiments, including a plan view (FIG. 17A) and a front side view (FIG. 17B). The dual-band camera system 1700 includes a housing 1702 with a cover 1704 enclosing the system components, which include an infrared camera 1710 (e.g., a LWIR camera), a beam splitter 1720, a visible-light camera 1730 and processing components 1740 (e.g., a GPU board). The dual-band camera system 1700 is configured to receive infrared waves 1706 and visible-light waves 1708 of a scene. The beamsplitter 1720 allows the visible-light waves 1708 to pass through to the visible-light camera 1730. In various embodiments, the visible-light camera 1730 includes optical components and/or separate optical components 1732 are provided to focus the visible-light 1708 for the image capture components of the visible-light camera 1730. The beamsplitter 1720 is also configured to reflect the infrared waves 1706 through window 1712 towards infrared camera 1710. Processing components 1740 are provided to warp the infrared images to overlay on the visible-light images and generate a two-channel, dual band video stream.

Screening for Elevated Body Temperature

Embodiments of the present disclosure for elevated body temperature screening (e.g., gate screening) will now be described with reference to FIGS. 18A-22E. In various scenarios and contexts, embodiments of the present disclosure can be utilized at any location where screening of temperature is desired, such as an entrance to buildings such as offices, malls, corporate and manufacturing facilities, etc. Various embodiments are directed to scenarios where scanning of one individual at a time (per camera) is performed, including screening of individuals at airports or other travel facilities.

Figure 18A:
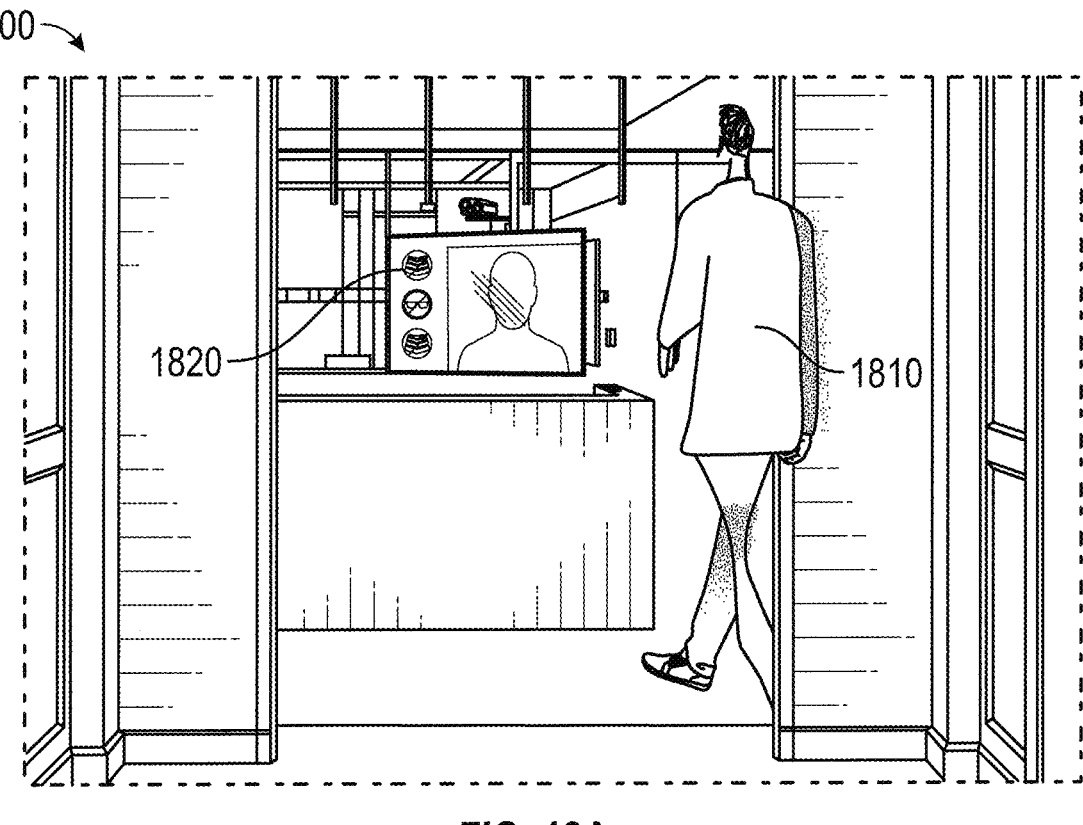
FIGS. 18A, 18B, and 18C illustrate an implementation of an elevated temperature system, in accordance with one or more embodiments.
Figure 18B:
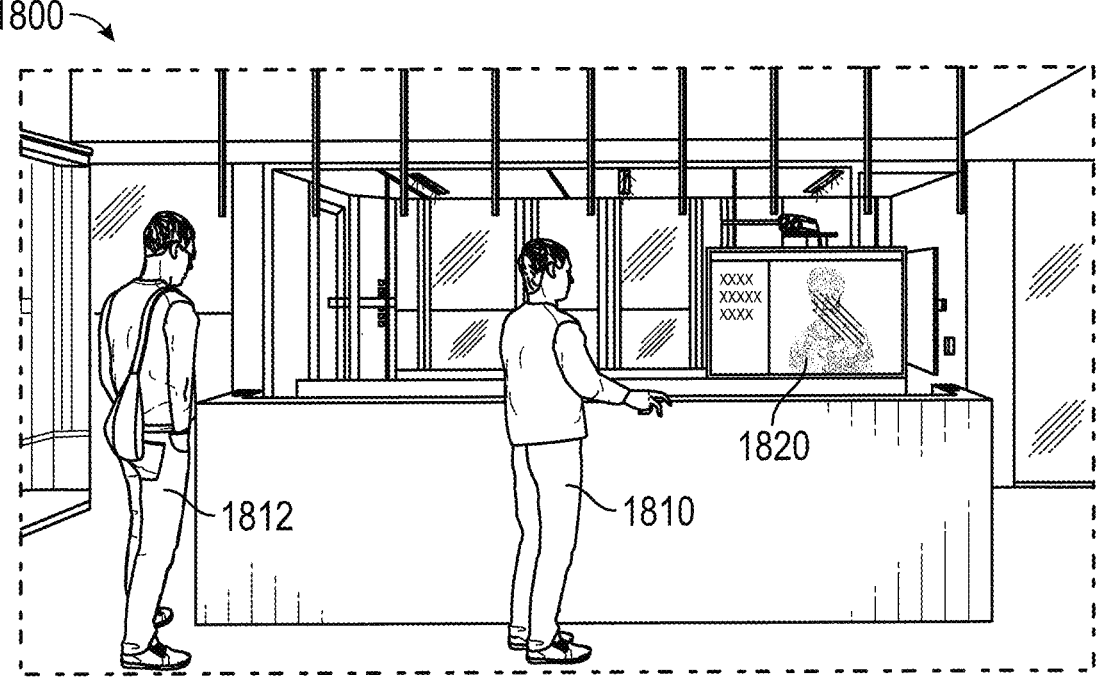

Various embodiments will now be described with reference to FIGS. 18A-C. FIGS. 18A-B illustrate an example elevated temperature testing area 1800, such as an entrance to a facility, such as building or office lobby, etc. The elevated temperature testing area 1800 includes a testing system 1820 set up at a check-in area. People entering the elevated temperature testing area 1800, such as person 1810 and person 1812 check-in one at a time through the testing system 1820.

Figure 18C:
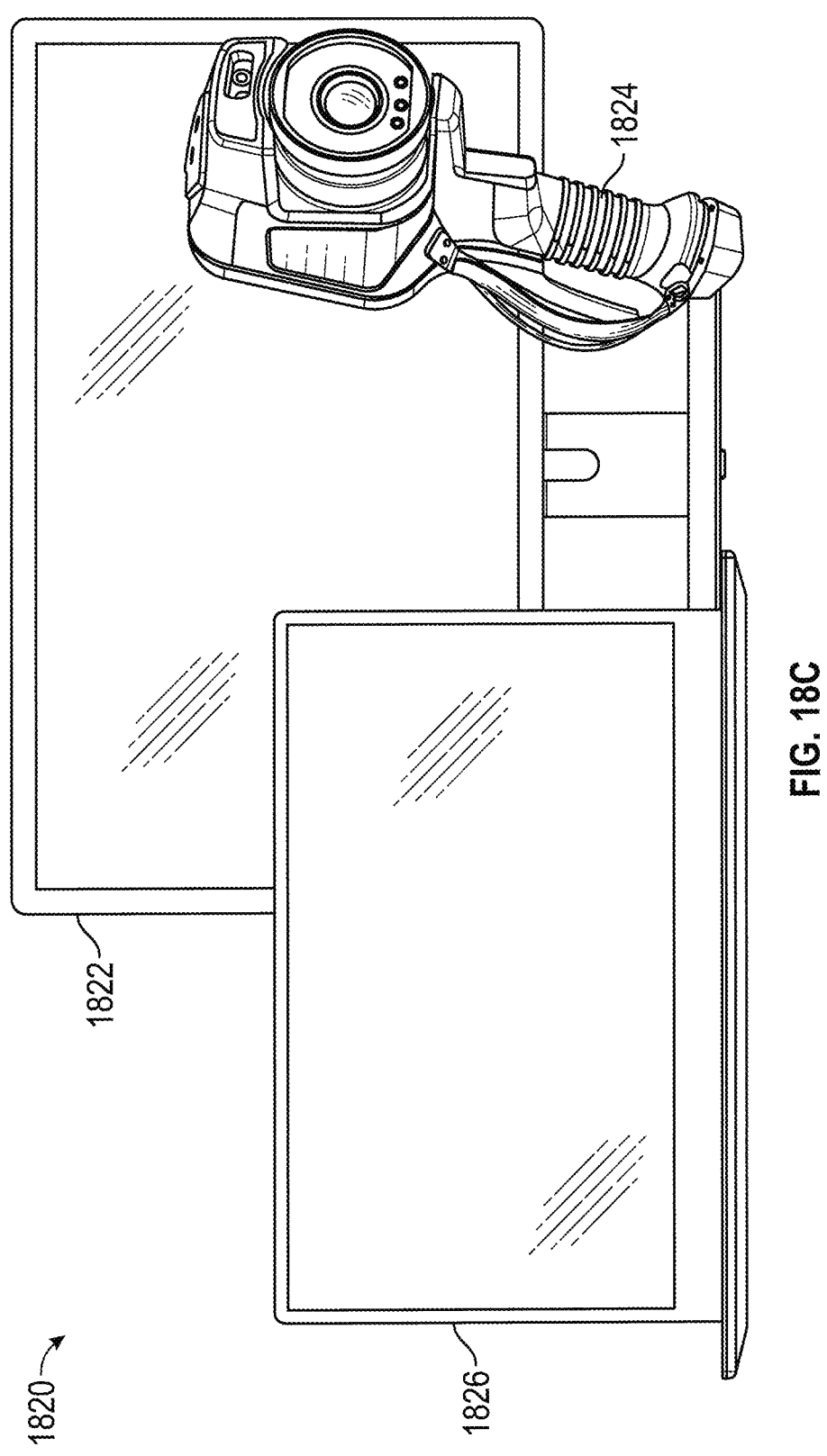

Referring to FIG. 18C, embodiments of a testing system 1820 will now be described. A testing system 1820 includes a display 1822 that may be configured to be visible to the person being tested, an infrared-imaging camera 1824 and a computing system 1826. In various embodiments, the testing system may be implemented using a dual band camera system providing both visible and infrared images of the person to be tested, such as the dual band camera systems described in FIGS. 1-17B.

In some embodiments, the system 1820 is implemented as a self-evaluating skin temperature scanning system, an example of which will now be described with reference to FIGS. 19A-G and 20. In order to aid a person in how to perform a scan, several aspects are evaluated to allow for a correct measurement result. The illustrated embodiment includes several steps and instructions that are communicated to the user via text, graphics and animations on the display.

Figure 19B:
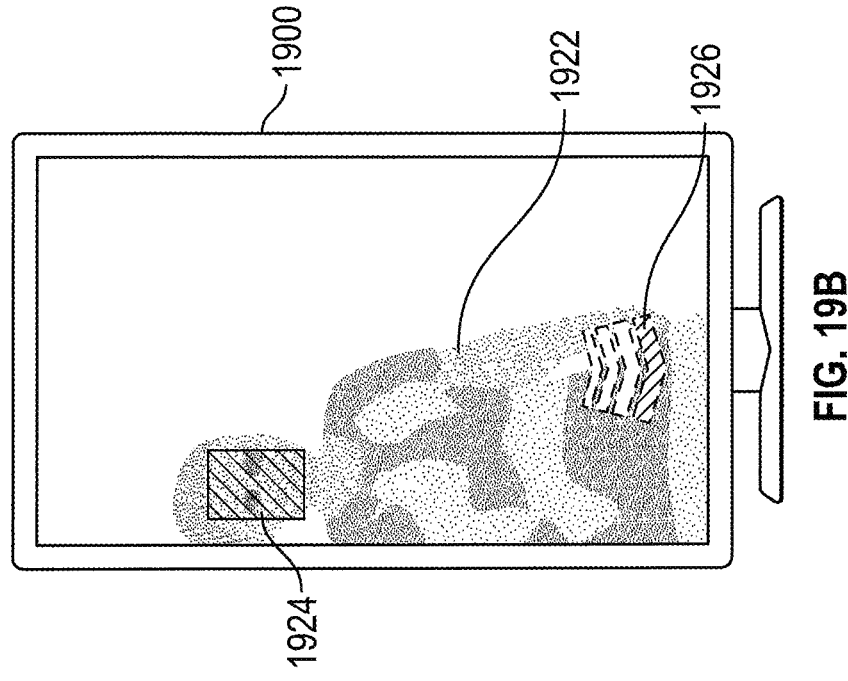
FIGS. 19A, 19B, 19C, 19D, 19E, 19F, and 19G, illustrate display views of an elevated temperature system, in accordance with one or more embodiments.
Figure 19A:
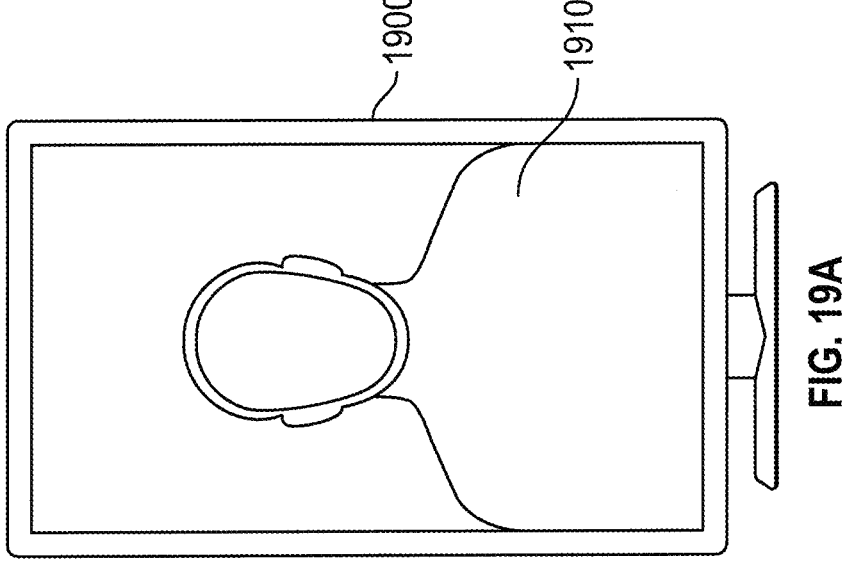

The scanning process 2000 begins in step 2010 with the display 1900 providing a visual indication to the user that they shall step in front of the infrared camera and place themselves towards the display. This may be done, for example, by displaying a silhouette 1910 as illustrated in FIG. 19A or similar graphics indicating that there should be a person standing in front of the monitor. In some embodiments, the infrared camera is mounted on or near the monitor and the monitor 1900 provides a view of both the silhouette 1910 and the user's image captured by the camera, allowing the user to position within the silhouette 1910. Referring to FIG. 19B, an example image 1920 of a person 1922 approaching the monitor 1900 (and camera) is provided. The person 1922 is imaged by the camera and the captured image is analyzed to detect the person's face. The size and location of the detected face 1924 in the image are analyzed to guide the person into the right position within the silhouette 1910. In the illustrated image, the person is standing too far away and a graphic 1926 on the screen is provided to guide the person into the proper position. For example, the graphic 1926 may include animated arrows directing the person 1922 to step closer for an accurate scan.

Figure 19D:
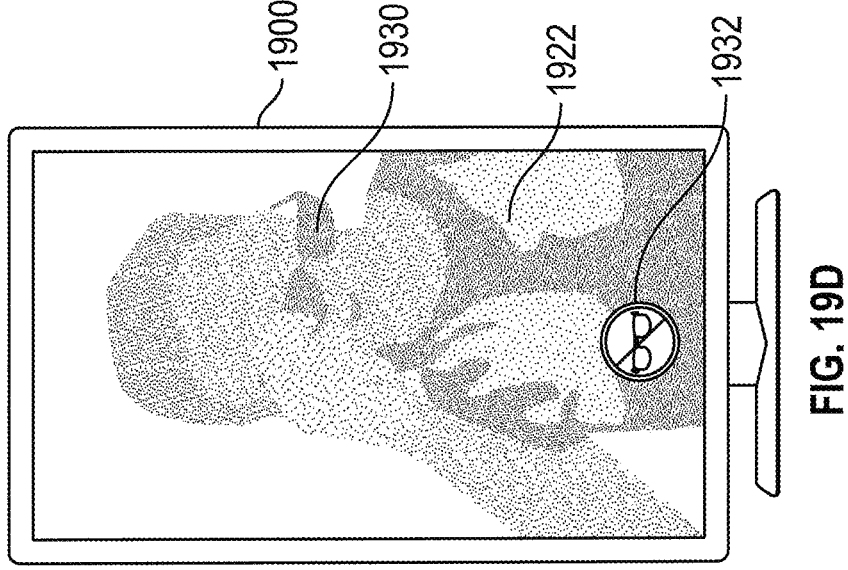
Figure 19C:
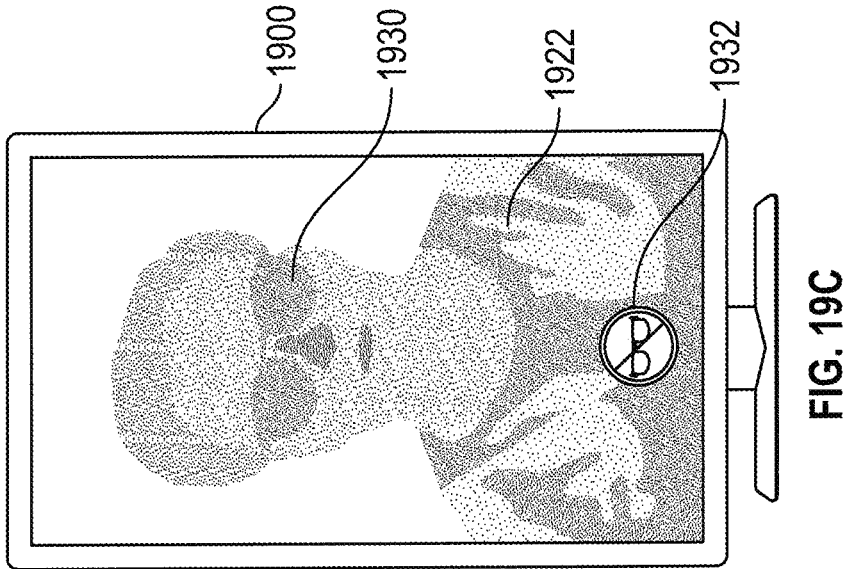

In step 2020, the system instructs the user to remove obstructing apparel, such as a hat, facemask, eye glasses or sunglasses. In various embodiments, the system captures images of the user, detects the user's face, and identifies whether obstructing apparel is present. Obstructing headwear, for example, can interfere with the temperature measurement performed by the IR technology, potentially causing the system to display an inaccurate result. Thus, the system automatically detects glasses or other headwear such as hats, facemasks etc. Depending on object detected, relevant graphics are displayed to the user, indicating that it must be removed. In some embodiments, the system includes a trained neural network configured to detect the presence of one or more obstructing objects. As illustrated in FIG. 19C, when an obstructing object is detected, the system may provide a graphic 1932 or other indication instructing the user to remove the obstructing object. In the illustrated embodiment, the user is wearing sunglasses 1930, which are detected by an image processing system and/or neural network, and a "remove glasses" graphics is provided to the user. The camera and image processing system monitor the user's face with a live infrared video stream, to detect the user's face and any obstructing apparel (e.g., the removal of sunglasses as illustrated in FIG. 19D) and detect when the user's face is in position for scanning.

Figures 19E, 19F, 19G:
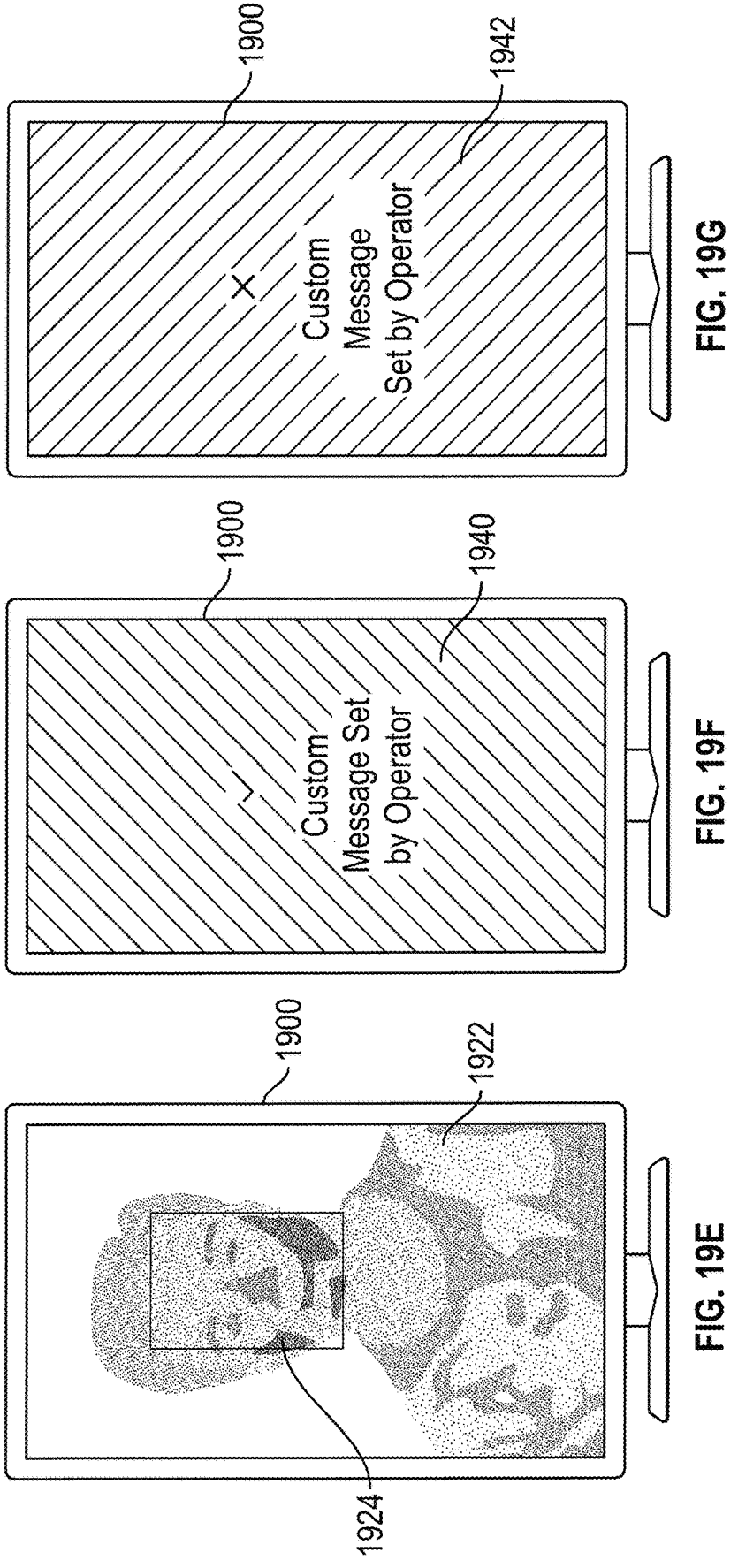
Figure 21B:
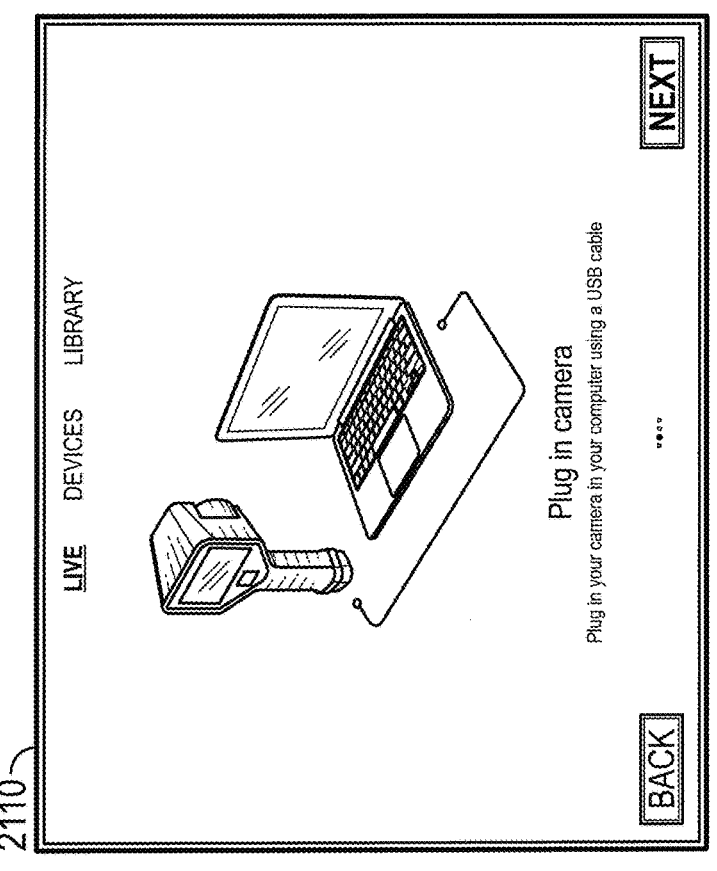
Figure 21A:
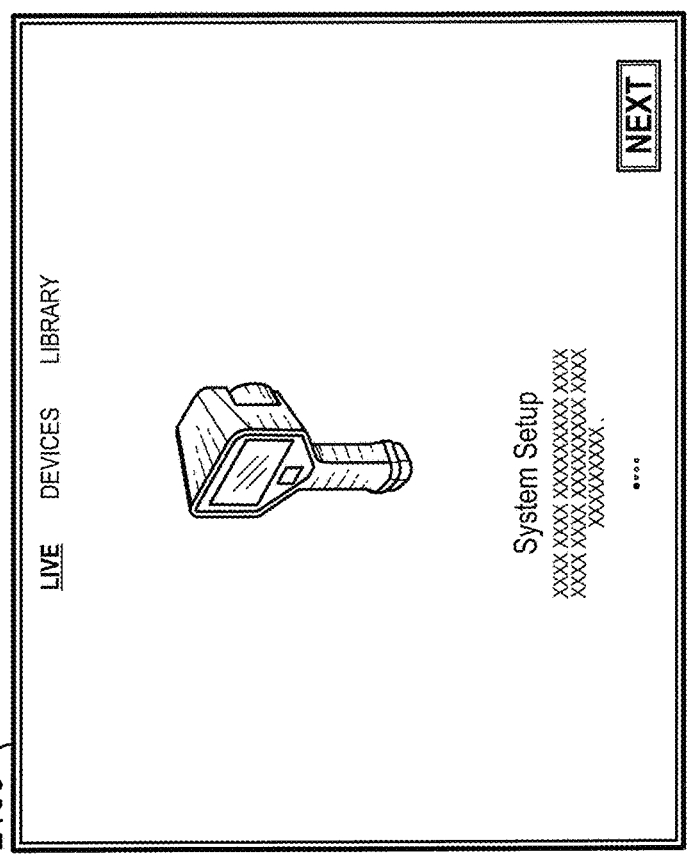
Figures 21E, 21F:
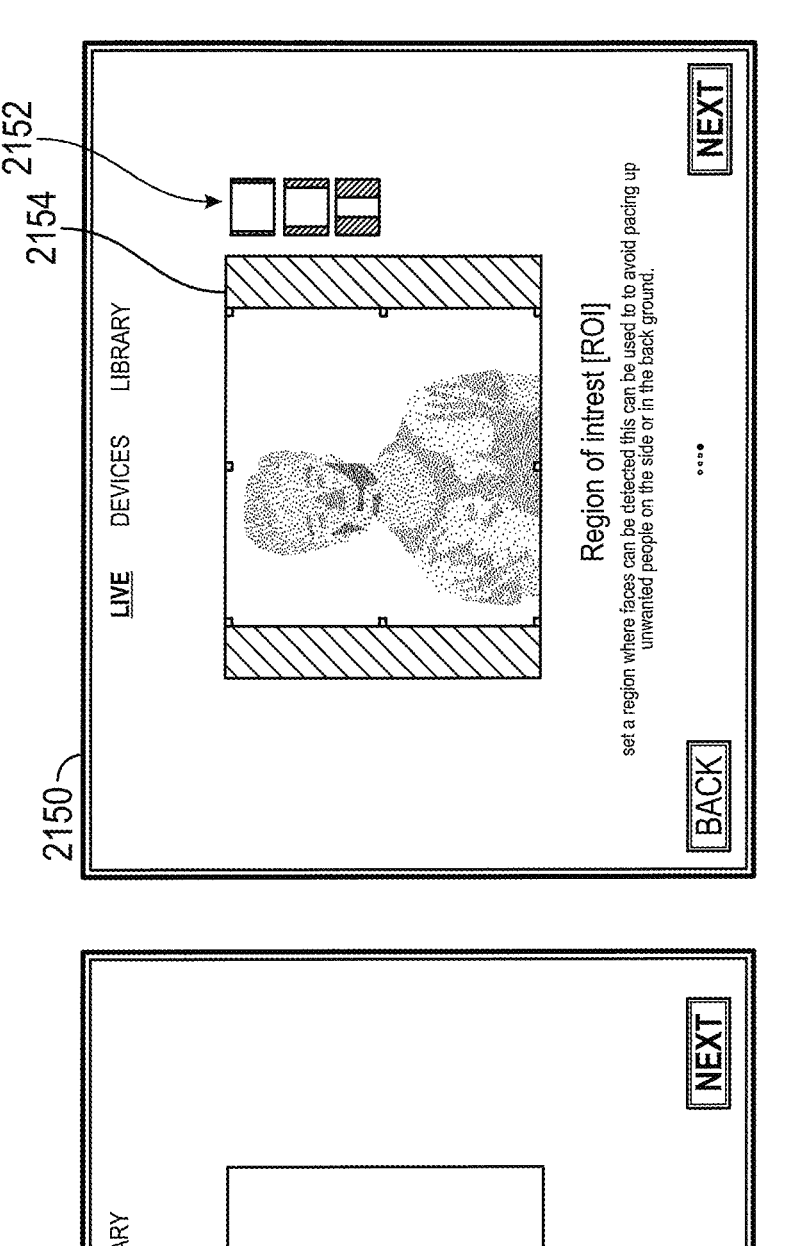

In step 2030, the system initiates the temperature scan of the user. In some embodiments, the system initiates a scan automatically when it identifies that certain criteria are met. For example, the system may track the user through image processing and/or other sensors to determine when the person is standing at the correct distance (e.g., that a large enough portion of the persons' face is being detected). The system may also verify that obstructing apparel is not covering the areas of the face to be measured (e.g., no headwear, glasses, facemasks or other apparel that is covering the face is detected). When the person is in the proper position and other criteria is met (e.g., as illustrated in FIG. 19E), the system indicates with visual and auditory feedback that it is ready to initiate a skin temperature scan.

In step 2040, the system determines a user temperature by evaluating the infrared image of the user when in proper position. If the user moves during measurement, the user may be asked to reposition as previously discussed and the process is repeated. In some embodiments, the system determines a measurement location, such as a forehead or tear duct, calculates a temperature at the measurement location, and compares the measured temperature to one or more thresholds to determine whether the person has an elevated body temperature.

In step 2050, the system displays a message and/or performs tasks in accordance with the measured temperature. For example, if the user does not deviate from the accepted temperature limit, he or she may receive a positive message (e.g., as illustrated in FIG. 19F; this message may be in green) communicating that they have been cleared from having an elevated temperature. The user may then be permitted to pass the check point and enter the facility according to facility protocols (e.g., wearing an employee or visitor badge). If the measured temperature deviates from what has been set as an accepted temperature, the user may receive a message (e.g., as illustrated in FIG. 19G; this message may be in red) communicating that they have an elevated body temperature. The written message in the result may be customizable to meet implementation requirements and can be specific for the system setup location and circumstances. For example, if the person has an elevated body temperature, the user may be denied entry to the facility, be instructed to meet with a doctor or other medical personnel, be instructed to isolate/quarantine (e.g., in an infectious disease outbreak), or take other precautionary steps.

System Setup and Installation

Because the accuracy of a scan of skin temperature with infrared technology depends on various settings and conditions, the present disclosure also provides a guide for an installer of the system in how to set it up for optimized measurement results. Sample user interface screens for a system installation are illustrated in FIGS. 21A-21F and will now be described. In some embodiment, the computer (e.g., computer 1826 of FIG. 18C) executes a setup routine to initialize the system for proper elevated body temperature measurements.

In screen 2100, the initialization system begins, providing a step-by-step guide for installing the system. In screen 2110, the user is instructed to plug in their camera to the computer via cable or other mode of communications. For example, in screen 2120 the user can also connect their camera to a Wi-Fi access point (either the computer itself or the same access point that the computer is connected to) in order to allow for remote streaming and connectivity. With the camera plugged into the computer, the system may be configured to detect which optics are used. For example, a suggested distance for performing a scan can be recommended as illustrated in screen 2130 to set up the camera in an optimal position with respect to an expected user measurement location.

In order to get good quality in the streaming IR image the user is prompted with in screen 2140 to set up the camera focus. This can either be done manually on the focus wheel of the camera hardware or by clicking "auto focus" in the digital user interface. Since the IR image is streaming continuously, the user will receive immediate feedback on the state of optical focus.

As illustrated in screen 2150, the user may further be prompted with a digital masking tool 2152 that will allow them to set the region of interest 2154 in the streaming IR image. The region of interest decides the area in which a face will be allowed to be detected. If a face is visible within the camera view but outside the set region of interest, it will not be detected. This feature can help avoid unwanted measurements of people passing by in the background of the person being scanned.

If the scanned person has a skin temperature that exceeds the accepted limit, the system will alert that an elevated temperature has been detected. During the setup the user may be prompted to set a margin based on temperature, that will allow for some deviation in the accepted temperature limit. For example, a screen may be presented prompting the user to "set temperature threshold" such as +2-degrees C., +1.5-degrees C., or +1-degree C. In various embodiments, the system allows the user to set the temperature margin when the system is being set up, in order to avoid potential errors that might occur if the user delays in setting up at a later stage in the use of the product.

Figure 22A:
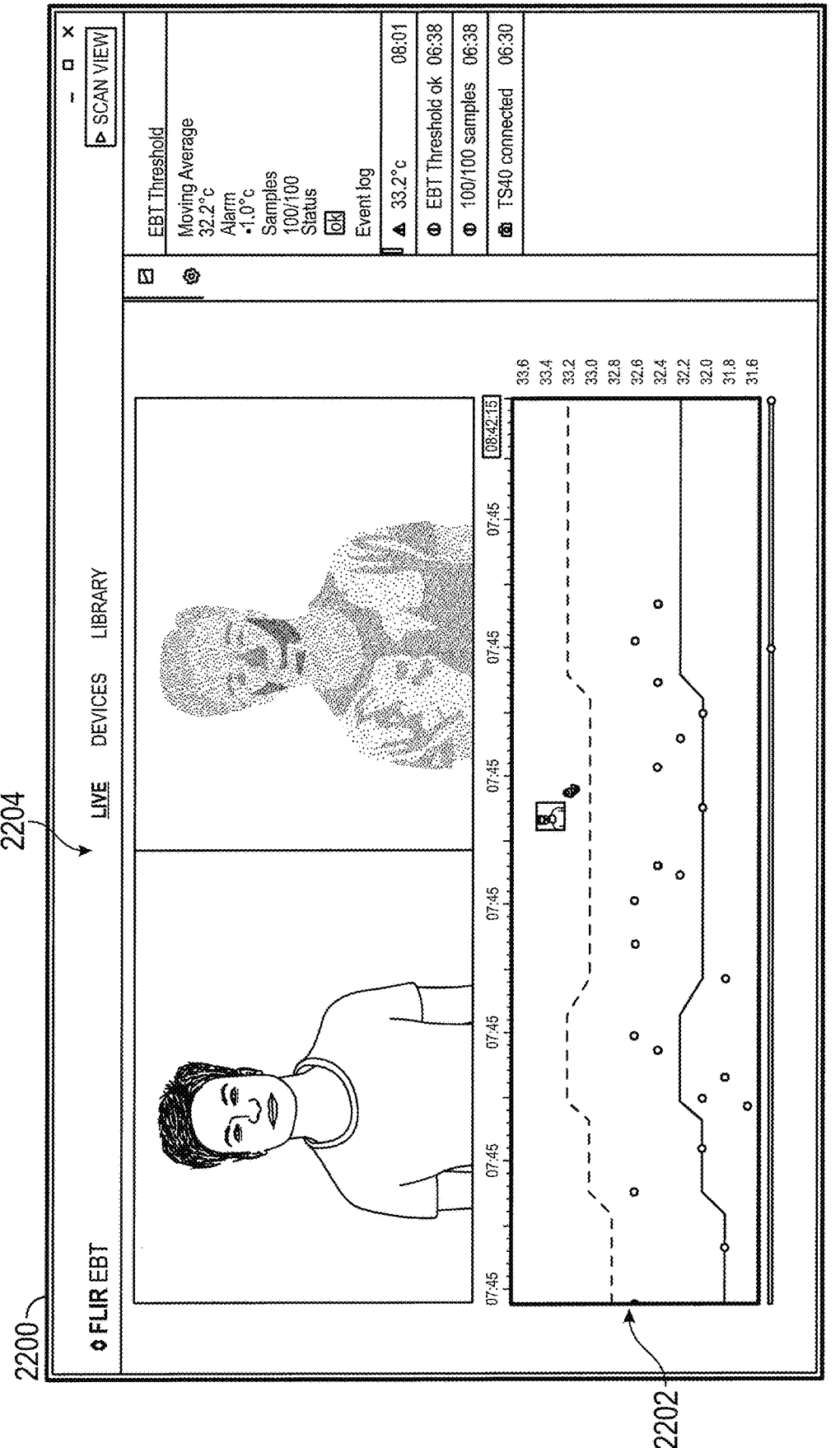
FIGS. 22A. 22B, 22C, 22D, and 22E, illustrates various operator views during system operation, in accordance with one or more embodiments.
Figure 22B:
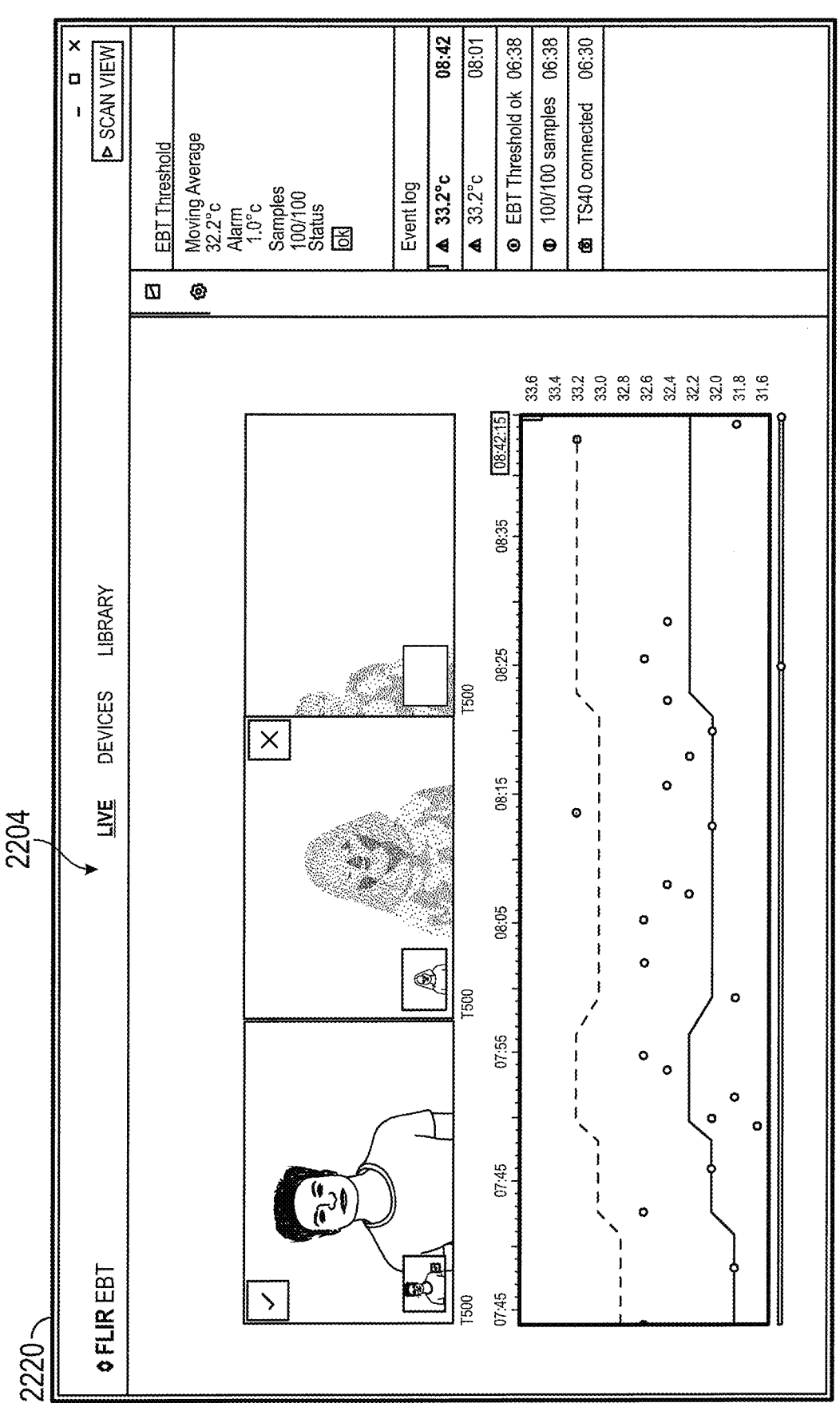
Figure 22C:
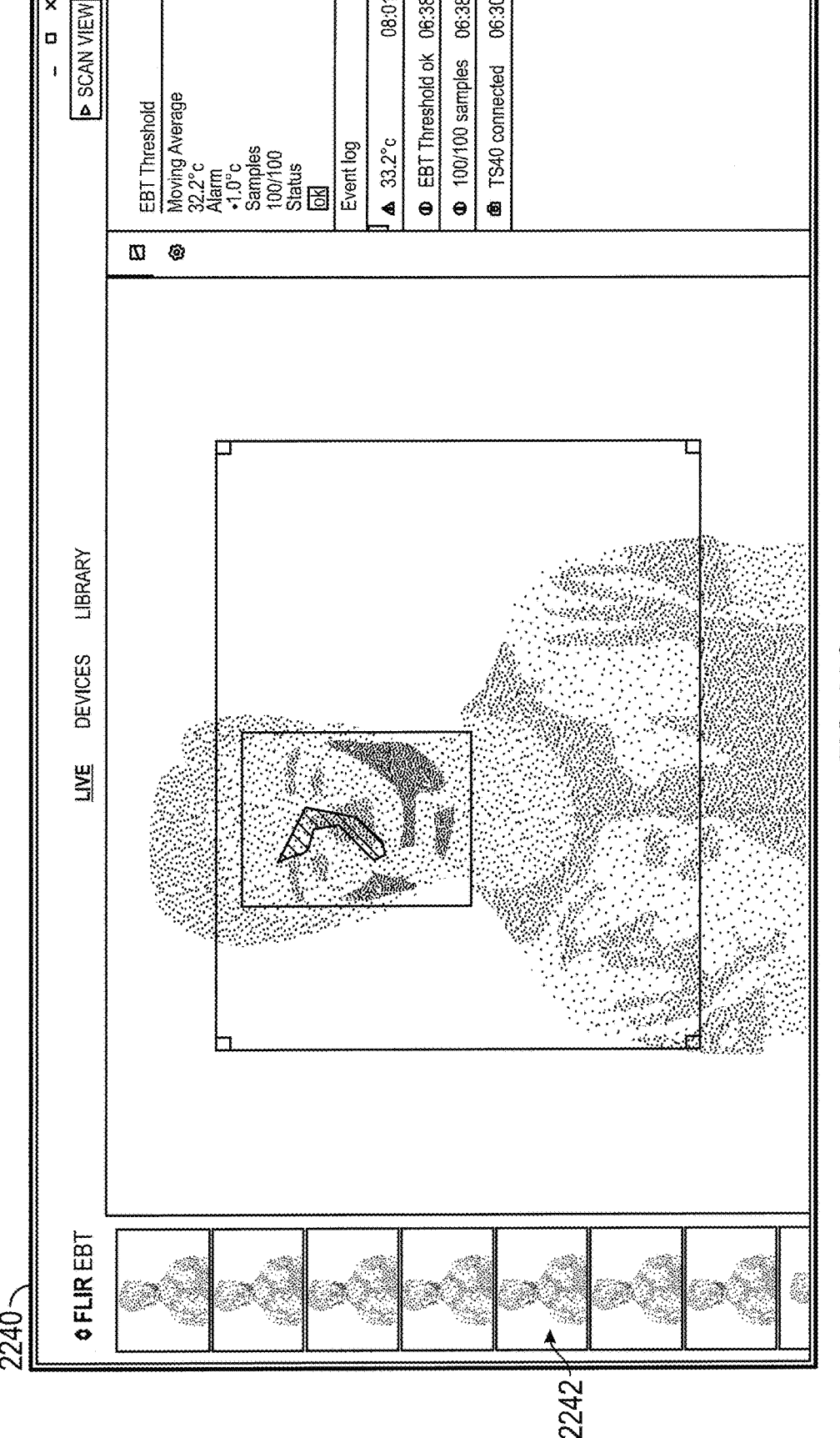

Aspects of the present disclosure further include an "operators view" 2200 presented on a display of the system (e.g., a display on the computer) where various settings and information are displayed. Sample display views are illustrated in FIGS. 22A-22E. As illustrated in FIG. 22A, the operator may be presented with a timeline of performed scans 2202 with the ability to see the measured temperatures and saved images 2204. This provides the possibility to see a historical view of the temperature curve. The user can click on any of the performed scans in order to see more details such as measured temperature, images and result. As illustrated in FIG. 22B, the operators view 2220 allows for several IR video streams to be shown at the same time through connecting multiple cameras to the system (e.g., systems that include multiple cameras to scan multiple people). The display 2240 (FIG. 22C) may further be configured to display images of scanned individuals 2242 that can be displayed and stored in local system, a remote system, a cloud database or other storage for further analysis.

Figure 22E:
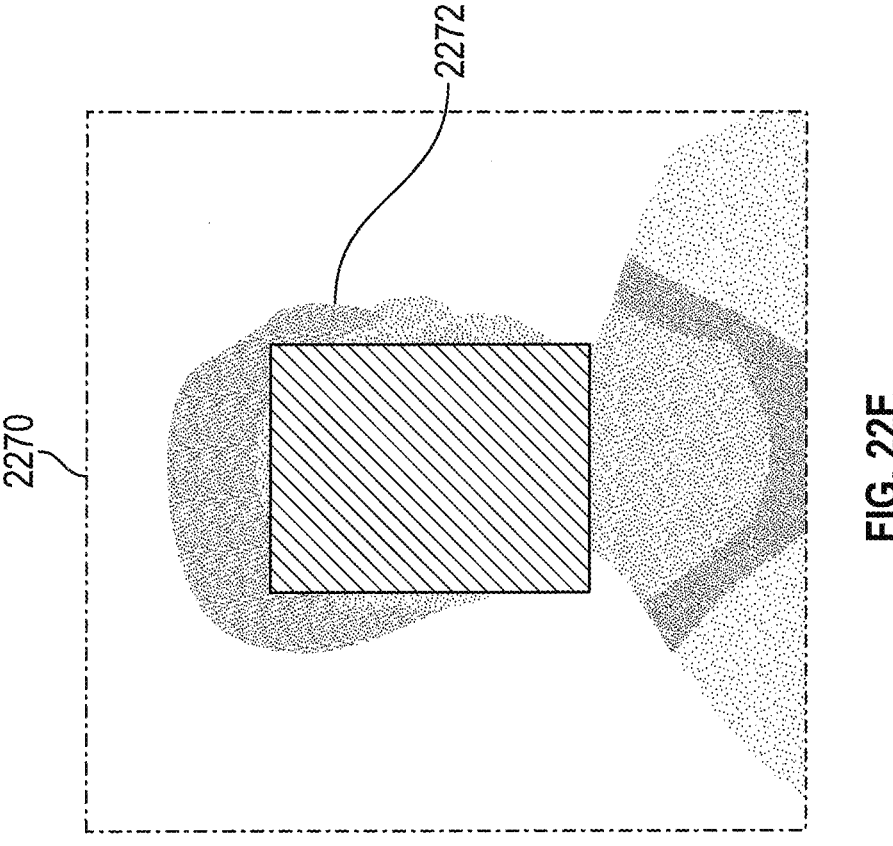
Figure 22D:
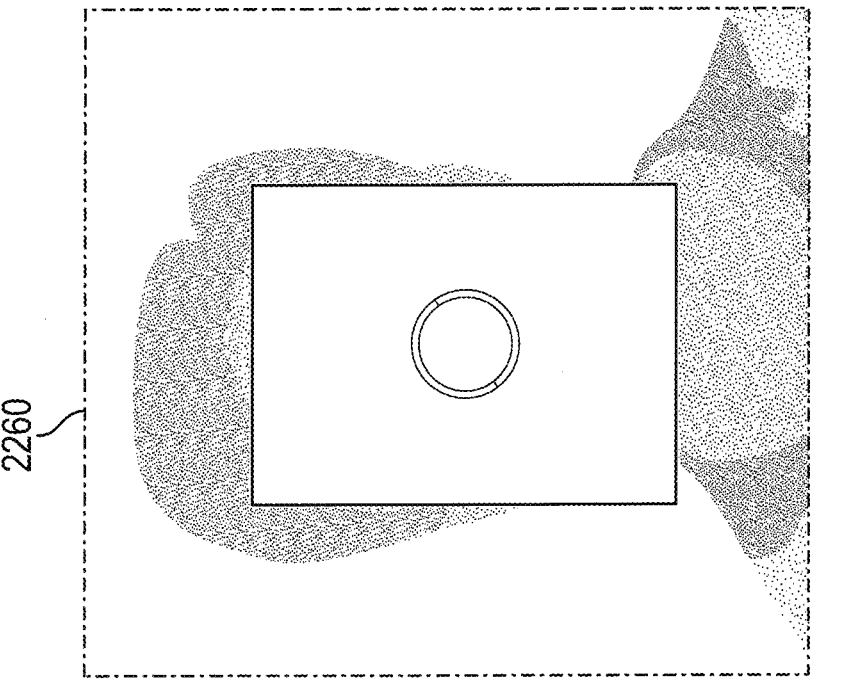

Referring to FIGS. 22D and 22E, the system may be configured to provide a blurred overlay to protect the integrity of the person (e.g., illustrated in display 2260) being scanned and provide a more comfortable experience to the user. A blurred overlay can be applied to the already existing graphics, such that the user can choose whether they want a transparent or blurred square to signal and follow the detected face.

To preserve the integrity of the scanned individual, he/she and the physical environment could be completely masked with computerized and virtual graphics as illustrated in display 2270. The surrounding environment such as walls, floors, ceiling, decorations etc. could be replaced with showing a plain background that has no visual connection to the physical world. Additionally, the person detected could be replaced with a virtual avatar (e.g., image 2272) that corresponds to his/her movements, reducing the feeling of being monitored but still providing understanding of where and how the person should move physically in order to perform a correct scan.

It will be appreciated that the present disclosure provides improved accuracy and consistency in elevated temperature measurement. The systems disclosed herein allow an untrained person to be guided to perform a thermal imaging skin temperature scan and interpret the result without the need of education or any prior knowledge about thermodynamics or infrared technology. With the help of instructions—text, sound and overlay graphics—the user receives relevant information about how to proceed with the scan to get a consistent and accurate result. The present disclosure also aids in the set-up of such a system, guiding the user through the process of installing the system to give a consistent and accurate result and therefore being able to avoid false negatives. The present disclosure utilizes step-by-step guidance to lower the threshold of use, enabling any person, company, organization, store or facility to utilize thermal imaging for detecting skin temperature. One strength lies in the simplicity, combining already existing hardware and technology with a sophisticated graphical user interface, orchestrated in such a way that it can be used and deployed with no requirements of certain knowledge or context.

Where applicable, various embodiments provided by the present disclosure can be implemented using hardware, software, or combinations of hardware and software. Also, where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure.

Software in accordance with the present disclosure, such as non-transitory instructions, program code, and/or data, can be stored on one or more non-transitory machine-readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. A method comprising:

scanning a region of interest using an infrared camera to produce a captured image;

detecting a person in the region of interest;

instructing the person to move into a scanning position for temperature scanning by the infrared camera;

initiating the temperature scanning of the person by the infrared camera if scanning criteria is satisfied;

determining temperature of the person and comparing to at least one temperature threshold; and performing a task associated with determined temperature;

wherein instructing the person to move into a scanning position comprises:

displaying a silhouette on a display screen, the silhouette corresponding to the scanning position;

determining a location of the person in the captured image; and instructing the person to position within the displayed silhouette;

wherein instructing the person to position within the displayed silhouette comprises displaying a motion direction by an indicator depending on the person's location in the captured image while displaying the person's movement on the display screen; and wherein displaying the person's movement on the display screen comprises displaying on the display screen both the silhouette and an infrared image of the moving person captured by the infrared camera.

2. The method of claim 1, wherein scanning a region of interest further comprises scanning the region of interest using a visible image camera.

3. The method of claim 2, further comprising providing a dual-image camera comprising the infrared camera and the visible image camera, wherein the dual-image camera comprises a beamsplitter arranged to reflect infrared light towards the infrared camera and pass through visible light to the visible image camera.

4. The method of claim 1, wherein detecting a person in the region of interest comprises detecting a face in the captured infrared image.

5. The method of claim 4, wherein instructing the person to move into a scanning position is performed based on analyzing a size and location of the detected face.

6. The method of claim 1, wherein displaying a motion direction comprises displaying a static and/or animated arrow.

7. The method of claim 1, wherein displaying a motion direction comprises displaying an animated graphic directing the person to move into a proper position; and determining a location of the person comprises determining that the person is standing in a position away from the scanning position.

8. The method of claim 1, further comprising detecting obstructing apparel in the captured image, classifying the obstructing apparel and instructing the user to remove the obstructing apparel based, as least in part, on the classification.

9. The method of claim 8, further comprising tracking the person through the captured infrared images to confirm removal of the obstructing apparel.

10. The method of claim 8, wherein the obstructive apparel includes a head covering, glasses and/or a facemask.

11. The method of claim 1, wherein the scanning criteria comprises the person being positioned within a displayed silhouette and no detected obstructing apparel.

12. The method of claim 1, wherein when the determined temperature of the person is greater than the at least one temperature threshold the person is determined to have a fever.

13. The method of claim 1, further comprising initializing a temperature measurement system comprising the infrared camera including guiding a user to arrange the infrared camera to be an optimal distance from the person and/or defining a region of interest in a field of view of the infrared camera.

14. The method of claim 1, further comprising obscuring the captured image of the person when displayed to an operator, including blurring a face displayed in the captured image and/or displaying an avatar representation of the person.

15. A system comprising:

an infrared camera configured to capture an infrared image of a scene;

a display configured to display a portion of the captured infrared image and at least one graphic indicia to guide a person being scanned; and a logic device configured to:

scan a region of interest using an infrared camera;

detect a person in the region of interest;

instruct the person to move into a scanning position for temperature scanning by the infrared camera;

initiate the temperature scanning of person by the infrared camera if scanning criteria is satisfied;

determine temperature of the person and compare to at least one temperature threshold; and perform a task associated with determined temperature;

wherein instructing the person to move into a scanning position comprises:

displaying a silhouette on a display screen;

determining a location of the person in the captured image; and instructing the person to position within the displayed silhouette;

wherein instructing the person to position within the displayed silhouette comprises displaying a motion direction by an indicator depending on the person's location in the captured image while displaying the person's movement on the display screen; and wherein displaying the person's movement on the display screen comprises displaying on the display screen both the silhouette and an infrared image of the moving person captured by the infrared camera.

16. The system of claim 15, further comprising a dual-image camera comprising the infrared camera and a visible image camera, wherein the dual-image camera comprises a beamsplitter arranged to reflect visible light towards the visible image camera and pass through an infrared image to the infrared camera.

17. The system of claim 15, wherein detecting a person in the region of interest comprises detecting a face in the captured infrared image.

18. The system of claim 17, wherein the logic device is further configured to instruct the person to move into a scanning position based on analyzing a size and location of the detected face.

19. The system of claim 15, wherein the logic device is further configured to instruct the person to move into a scanning position by displaying an animated graphic directing the person to move into a proper position; and determining a location of the person comprises determining that the person is standing in a position away from the scanning position.

20. The system of claim 15, wherein the logic device is further configured to detect obstructing apparel in the captured infrared image, classify the obstructing apparel and instruct the person to remove the obstructing apparel based, as least in part, on the classification.

* * * * *